US009052314B2

(12) United States Patent
DiNello et al.

(10) Patent No.: US 9,052,314 B2
(45) Date of Patent: Jun. 9, 2015

(54) BIOMARKERS FOR DETECTING THE PRESENCE OF BACTERIA

(71) Applicant: Silver Lake Research Corporation, Monrovia, CA (US)

(72) Inventors: Robert K. DiNello, Alhambra, CA (US); Mark Geisberg, Arcadia, CA (US)

(73) Assignee: SILVER LAKE RESEARCH CORPORATION, Monrovia, CA (US)

( * ) Notice: Subject to any disclaimer, the term of this patent is extended or adjusted under 35 U.S.C. 154(b) by 0 days.

(21) Appl. No.: 13/828,554

(22) Filed: Mar. 14, 2013

(65) Prior Publication Data
US 2014/0273022 A1    Sep. 18, 2014

(51) Int. Cl.
| | |
|---|---|
| *G01N 33/554* | (2006.01) |
| *G01N 33/569* | (2006.01) |
| *G01N 33/53* | (2006.01) |
| *C12Q 1/00* | (2006.01) |
| *C12Q 1/04* | (2006.01) |
| *C12Q 1/16* | (2006.01) |
| *C12Q 1/14* | (2006.01) |
| *C12M 1/34* | (2006.01) |
| *C12M 3/00* | (2006.01) |
| *G01N 33/68* | (2006.01) |
| *C07K 16/12* | (2006.01) |

(52) U.S. Cl.
CPC .... *G01N 33/56911* (2013.01); *G01N 33/56916* (2013.01); *G01N 33/56922* (2013.01); *G01N 33/56927* (2013.01); *G01N 33/56933* (2013.01); *G01N 33/56938* (2013.01); *G01N 33/56944* (2013.01); *G01N 33/5695* (2013.01); *G01N 33/6854* (2013.01); *C07K 16/1203* (2013.01); *C07K 16/1232* (2013.01); *C07K 2317/30* (2013.01); *C07K 2317/34* (2013.01)

(58) Field of Classification Search
None
See application file for complete search history.

(56) References Cited

U.S. PATENT DOCUMENTS

| | | | | |
|---|---|---|---|---|
| 4,168,146 | A | 9/1979 | Grubb et al. | 435/7.92 |
| 4,435,504 | A | 3/1984 | Zuk et al. | 435/7.91 |
| 4,740,468 | A | 4/1988 | Weng et al. | 435/7.91 |
| 4,861,711 | A | 8/1989 | Friesen et al. | 435/7.92 |
| 4,959,307 | A | 9/1990 | Olson | 435/7.91 |
| 5,141,875 | A | 8/1992 | Kelton et al. | 436/514 |
| 5,591,645 | A | 1/1997 | Rosenstein | 436/514 |
| 6,136,610 | A * | 10/2000 | Polito et al. | 436/514 |
| 6,872,398 | B2 * | 3/2005 | Castric et al. | 424/242.1 |
| 7,919,331 | B2 | 4/2011 | Geisberg | 436/514 |
| 2003/0059839 | A1 * | 3/2003 | Obiso et al. | 435/7.1 |
| 2014/0227314 | A1 * | 8/2014 | Donnenberg | 424/190.1 |

FOREIGN PATENT DOCUMENTS

| | | |
|---|---|---|
| EP | 290 194 | 11/1988 |
| EP | 291194 | 11/1988 |
| EP | 323605 | 7/1989 |
| WO | WO 92/12428 | 7/1992 |
| WO | WO 97/23600 | * 7/1997 |
| WO | WO 2006/138527 | 12/2006 |
| WO | WO 2010/135585 | 11/2010 |

OTHER PUBLICATIONS

Baynham et al., Journal of Bacteriology, 2006; 188(1): 132-140.*
Greenspan et al. (Nature Biotechnology 17: 936-937, 1999).*
Altschul, Nucleic Acids Res. 25:3389-3402, 1997.
Bennett, et al., J Immunol Meth. 153:31-40, 1992.
Bennett, et al., Lett App Microbiol. 22: 237-243, 1996.
Chibata, "Immobilized Enzymes." Halstead Press, NY (1978), list of contents only.
Craig, et al., Curr Opin Struct Biol 18(2):267-77, 2008.
Cutrecasas, J. Bio. Chem., 245:3059, 1970.
Doyle, Int J Food Microbiol. 12(4):289-301, 1991.
Dupont B, ed. Immunobiology of HLA. Histocompatibility Testing 1987, vol. I, and Immunogenetics and Histocompatibility, vol. II. Springer-Verlag, New York, 1988, contents only.
Elia, Current Protocols in Protein Science 3.6.1-3.6.21, 2010.
Evans, et al., Rev Infect Dis. 5 Suppl 4:S692-701, 1983.
Frens, Phys. Sci. 241:20-22, 1973, Nature Phys. Sci.
Harlow E, Lane D, Antibodies: A Laboratory Manual (Cold Spring Harbor, NY: CSHL Press, 1988, contents only.
Histocompatibility Testing: Report of a Conference and Workshop. Washington DC: National Academy of Sciences—National Research Council, 1964.
Kim & Doyle, Appl. Env. Microbiol. 58:1764-1767, 1992.
Landsteiner K. The Specificity of Serological Reactions, rev. edn. New York: Dover, 1962, contents.
Laster, et al., Clin Immunol Immunopathol. 44(2):187-205, 1987.
Mar. et al., Anal. Biochem., 60:149, et seq, 1974.
Marchler-Bauer, et al. Nucleic Acids Res. 39(D)225-9, 2011.
Martin, et al., N Engl J Med. 348:1546-1554, 2003.
Mattick, Annu Rev Microbiol. 56:289-314, 2002.
Millipore Corp., Short Guide for Developing Immunochromatographic Test Strips Bedford, MA, 1996.
Moyes, Current Protocols in Microbiology. 15:A.3K.1-A.3K.13, 2009.
Muso & Jacob, Clin Immunol Immunopathol. 42(3):370-4, 1987.
Niemeyer. Bioconjugation Protocols: Strategies and Methods. Humana Press, NJ. 2004, contents.
Orskov I, et al., Bacteriol Rev. 41(3):667-710, 1977.
Orskov, et al., Can J Microbiol. 38(7):699-704, 1992.

(Continued)

*Primary Examiner* — Gary Nickol
*Assistant Examiner* — Lakia Tongue
(74) *Attorney, Agent, or Firm* — Norton Rose Fulbright US LLP; Scott D. Rothenberger; Tamsen Barrett

(57) ABSTRACT

In some aspects, provided are methods relating to the use of bacterial N-methyl-2 superfamily proteins as a biomarker for the presence of bacteria in a sample. The invention also relates to novel methods of diagnosis of the presence of bacteria in a liquid or solid sample, detection of bacterial infections in humans or animals, and use of antibodies or other specific binding molecules capable of binding to N-methyl-2 superfamily proteins.

36 Claims, No Drawings

(56) References Cited

OTHER PUBLICATIONS

Parham & Brodsky, Hum Immunol. 3(4):277-99, 1981.
Pfaller, et al., Antimicrob Agents Chemother. 42(7):1762-70, 1998.
Pisetsky, et al., J Immunol. 143(11):3609-13, 1989.
Reier-Nilsen, et al., BMC Pediatr. 19;9:5, 2009.
Ryan KJ; Ray CG (editors) (2004). Sherris Medical Microbiology (4th ed.). McGraw Hill.
Serban, et al., J Immunol. 135(5):3122-7, 1985.
Sigrist, et al., Nucleic Acids Res. 38(Database issue)161-6, 2010.
Slot & Geuze, Eur. J. Cell Biol. 38:87-93, 1985.
Tijssen et al., Practice and Theory of Enzyme Immunoassays, Chapter 3, Elsevier Science Publishers, (1985).
Turkevich, et al., Discuss Faraday Soc. 11:55-75, 1951.
Versalovic, J, ed. Manual of Clinical Microbiology, 10th ed. ACM Press; 2011. Online edition.
Warren, et al., Clin Infect Dis. 29(4):745-58, 1999.
Weiss, IVD Technology, 48, 1999.
Wisdom, Methods in Molecular Biology. 295:131-4, 1994, actually pp. 123-126.
Wong R, Tse H, eds. "Lateral Flow Immunoassay" Humana Press, New York, NY. 2009.
Oliver & Jamur, "Immunocytochemical Methods and Protocols," $3^{rd}$ Ed (Methods in Molecular Biology vol. 588) Humana Press. DOI: 10.1007/978-1-59745-324-0, ISBN: 1588294633, 2009.
Giron. et al "Monoclonal Antibodies Specific for the Bundle-Forming Pilus of Enteropathogenic *Escherichia coli*", Infection and Immunity, Dec. 1995, vol. 63, No. 12, pp. 4949-4952.
International Search Report from related PCT Application PCT/US2014/018001, dated Jun. 4, 2014, 13 pages.

* cited by examiner

BIOMARKERS FOR DETECTING THE PRESENCE OF BACTERIA

BACKGROUND OF THE INVENTION

I. Field of the Invention

Embodiments of this invention are directed generally to the field of the use of biomarkers and bacteria. In certain aspects the invention is directed to methods for detecting bacterial contamination in samples by detecting a protein in the N-methyl-2 superfamily.

II. Description of the Related Art

The detection of bacteria is important in medical and veterinary microbiology, food safety, drinking water treatment, and many other areas. In particular, diagnosis of bacterial infections by detecting the causative bacteria is crucial to treatment of these common diseases.

Methods to diagnose the presence of bacteria include laboratory culture of samples to allow growth of the infectious agent on nutrient medium; detection of bacterial DNA sequences by polymerase chain reaction (PCR) or other methods; and direct detection of bacteria by chemical dyes and stains followed by microscopic examination (Ryan 2004). Major drawbacks of these methods include the laborious nature of the techniques and the time required to obtain a result—often more than a day in a typical laboratory. Most techniques also require a sample to be collected and transported to a laboratory capable of performing the test, adding additional time to obtain a result. In addition, some techniques require a pre-selection of which strains or species can be detected by a particular assay—for example, PCR detection necessitates the use of specific DNA sequences from bacterial species suspected of being present.

Immunoassays using specific antibodies binding to bacterial determinants are also known. These immunoassays are generally used following the culture of a particular sample to expand the number of bacteria present. In most such immunoassays, the antibodies are specific to particular strains of bacteria, serving to identify whether a population of bacteria contains a particular strain—often related to the serotype antigenic classification. Specific immunoassays exist to identify *E. coli* O157:H7 and other pathogenic strains (Kim 1992; Bennett; 1996).

For example, lateral flow immunochromatographic tests exist that detect the presence of *E. coli* O157:H7 in food and agricultural products following enrichment culture of any bacteria present (Neogen Corporation, Lansing, Mich.) (Kim 1992). This assay detects only a narrow range of enterotoxic *E. coli* strains. The assay uses antibodies specific for the O157 and H7 determinants, neither of which is a member of the N-methyl-2 superfamily. Another example of immunoassays detecting bacteria is the Premier™ ELISA detecting *Clostridium difficile* in stool specimens (Meridian Bioscience, Cincinnati, Ohio). This assay uses the enzyme glutamate dehydrogenase (GDH) as the biomarker for the presence of *Clostridium difficile* in stool samples, and comprises antibodies capable of binding to GDH. GDH is not a member of the N-methyl-2 superfamily. Another example is the Watersafe® Bacteria Test (SLRC, Monrovia, Calif.), a lateral flow immunochromatographic test strip detecting high levels of some strains of *E. coli* and *Pseudomonas aeruginosa* in swimming pools. This test uses monoclonal antibodies that are not specific for proteins of the N-methyl-2 superfamily.

However, there remains a need for methods to detect a broad range bacteria in a sample.

SUMMARY OF THE INVENTION

In some aspects, provided are methods relating to the use of bacterial N-methyl-2 superfamily proteins as a biomarker for the presence of bacteria in a sample. The invention also relates to novel methods of diagnosis of the presence of bacteria in a liquid or solid sample, detection of bacterial infections in humans or animals, and use of antibodies or other specific binding molecules capable of binding to N-methyl-2 superfamily proteins. In some embodiments, the disclosed methods provide processes for rapid detection of bacteria in samples with no culturing needed.

In some aspects, provided are methods of detecting the presence of bacteria in a sample comprising: (a) contacting the sample with an antibody, fragment thereof, aptamer or ligand capable of binding a protein in the N-methyl-2 superfamily to form one or more complexes in the presence of the N-methyl-2 superfamily proteins, if any, in the sample; and (b) detecting the presence of the one or more said complexes, wherein the presence of at least one complex indicates the presence of bacteria. In other aspects, provided are methods of detecting the bacterial contamination in a sample comprising: (a) contacting the sample with an antibody, fragment thereof, aptamer or ligand capable of binding a protein in the N-methyl-2 superfamily to form one or more complexes in the presence of the N-methyl-2 superfamily proteins, if any, in the sample; and (b) detecting the one or more said complexes, wherein the presence of at least one complex indicates the presence of a contaminating concentration of bacteria. In some aspects, provided are methods of identifying the presence of one or more specific bacteria in a sample comprising: (a) contacting the sample with an antibody, fragment thereof, aptamer or ligand capable of binding an identified protein of the N-methyl-2 superfamily expressed by a subset of bacteria but not by other bacteria to form one or more complexes in the presence of the one or more specific N-methyl-2 superfamily proteins, if any, in the sample; and (b) detecting the presence of the one or more said complexes, wherein the presence of at least one complex indicates the presence of the one or more specific bacteria.

In some embodiments, the protein in the N-methyl-2 superfamily has the conserved domain annotated as CDD c106830. In some embodiments, the protein in the N-methyl-2 superfamily comprises a conserved domain having the amino acid sequence of [KRHEQSTAG]-G-[FYLIVM]-[ST]-[LT]-[LIVP]-E-[LIVMFWSTAG] (SEQ ID NO. 1).

The antibody, fragment thereof, aptamer or ligand capable of binding a protein in the N-methyl-2 superfamily may be any appropriate form. In some embodiments, the antibody is polyclonal or monoclonal. In some embodiments, the antibody fragment is selected from the group consisting of a single-chain Fv, an Fab, an Fab', and an F(ab')2. In some embodiments, the antibody, fragment thereof, or aptamer is labeled. In some embodiments, the label is biotin, an enzyme, a latex particle, a metal colloid particle, a fluorescent dye, a quantum dot, or a carbon nanotube. In some embodiments, the antibody is CH1822 or CH1826.

The sample may be any appropriate sample. In some embodiments, the sample is a liquid sample. In some embodiments, the liquid sample is urine, blood, serum, blood products, plasma, saliva, body fluid, water, culture medium, diluted culture medium, petroleum product, fuel, liquid undergoing fermentation, or a beverage. In some embodiments, the sample is a solid sample. In some embodiments, the solid sample is human or animal tissue, stool, sputum, expectorate, an agricultural product, food, solids collected by centrifugation or filtration, soil, or sediment. In some embodiments, the solid sample is partially or completely solubilized by addition of liquid. In some embodiments, the sample is obtained from a human or an animal.

The detecting may be performed by any appropriate method known to those of skill in the art. In some embodiments, the detecting is performed by an immunoassay, an enzyme-linked immunosorbent assay (ELISA), an immunofluorescence assay (IFA), a radioimmunoassay (RIA), a chemiluminescence immunoassay (CLIA), a lateral flow chromatographic test, a Western blot, an immunoprecipitation assay, flow cytometry, or fluorescence microscopy. In some embodiments, the one or more antibodies are immobilized on a solid support. In some embodiments, the solid support is a particle, a bead, a plastic or glass surface, a porous membrane, an array, or a chip. In some embodiments, the solid support forms part of an assay device. In some embodiments, the assay device is a lateral flow immunoassay device.

The bacteria may be any bacteria that displays bacterial N-methyl-2 superfamily proteins on its surface. In some embodiments, the bacteria is of a genus selected from the group consisting of *Bacillus, Clostridium, Pseudomonas, Xanthomonas, Vibrio, Bacteroides, Escherichia, Klebsiella, Salmonella, Shigella, Erwinia, Rickettsia, Chlamydia, Mycoplasma, Actinomyces, Streptomyces, Mycobacterium, Micrococcus, Staphylococcus, Lactobacillus, Diplococcus, Streptococcus, Proteus, Citrobacter, Providencia, Morganella, Campylobacter, Gardnerella*, and *Borrelia*. In some embodiments, the bacteria is not isolated.

In some aspects, provided are kits for detecting bacteria in a sample suspected of containing bacteria comprising an antibody, fragment thereof, or aptamer capable of binding a protein in the N-methyl-2 superfamily. In some embodiments, the kit further comprises a solid substrate, wherein the antibody, fragment thereof, or aptamer capable of binding a protein in the N-methyl-2 superfamily is immobilized on the surface of the solid substrate. In some embodiments, the solid support is a particle, a bead, a plastic or glass surface, a porous membrane, an array, or a chip. In some embodiments, the kit further comprises a negative control, a positive control, or both.

"Biomarker" as used herein is a measurable characteristic indicative of a biological state. More specifically, a biomarker is a molecule, the concentration of which is measurable and directly related to the biological state, namely the presence of bacteria in a sample.

The use of the word "a" or "an" when used in conjunction with the term "comprising" may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. in relation to the total composition. The compositions and methods for their use can "comprise," "consist essentially of," or "consist of" any of the ingredients or steps disclosed throughout the specification.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

Described herein is an improved strategy for the detection of bacteria based on the use of a specific biomarker. This biomarker, comprising any of the proteins of the N-methyl-2 superfamily, is present on the surface of a large number of bacterial species and strains.

Also described are assays and methods for the rapid detection of bacteria based on biomarkers capable of binding to members of the N-methyl-2 superfamily, as well as uses of these assays in a variety of settings, including but not limited to drinking water samples suspected of containing bacteria, patient samples to detect the presence of bacterial infection in the patient, and food and beverage samples to detect bacterial contamination. All of the major bacterial pathogens are known to express N-methyl-2 superfamily proteins, including Type IV pilins. Examples of N-methyl-2 superfamily proteins from these species in the National Center for Biotechnology Information (NCBI) protein database include: YP_149493.1 (*Salmonella*); ZP_16921714.1 (*Clostridium perfringens*); ZP_09349343.1 (*Campylobacter* sp.); NP_374654.1 (*Staphylococcus aureus*); and ZP_12509418 (*Escherichia coli*). The ubiquity of this protein superfamily in bacteria makes it an attractive biomarker candidate for the detection of bacterial contamination.

A. N-Methyl-2 Superfamily

The N-methyl-2 superfamily, annotated in the Conserved Domains Database as #cl06830 (Marchler-Bauer 2011), is defined by a cleavage and methylation motif near the N-terminus, the processing of which generates a mature protein with a methylated N-terminal amino acid. The N-terminal cleavage and methylation site is described by PROSITE motif PS00409 as [KRHEQSTAG]-G-[FYLIVM]-[ST]-[LT]-[LIVP]-E-[LIVMFWSTAG] (SEQ ID NO. 1) (Sigrist 2010).

Many members of the N-methyl-2 superfamily are the major components of bacterial extracellular structures variously described as Type II secretion systems, Type IV pili, fimbriae, and other terms. Because such features are present in many species and strains of bacteria, investigators have assigned different nomenclature to the members of the N-methyl-2 superfamily, often without regard to the homology and common function of these proteins. In *Escherichia coli* alone, the proteins containing motifs placing them in the N-methyl-2 superfamily are variously termed PilA, Type IV pilin, prepilin peptidase-dependent protein D, PpdD, major pilin subunit, major fimbrial subunit, as well as many "putative" or less specific terms.

"PilA" refers to any member of the class of fibrous proteins that are major structural subunits of bacterial pili or fimbriae. PilA is also sometimes termed "fimbrial subunit", "fimbrial protein", "major PilA subunit", "major fimbrial subunit", and other terms. Genes encoding PilA proteins include ppdD, PilA, and thousands of other homologs across bacterial strains. PilA is the major extracellular component of Type IV pili. Type IV pili have been found on a large number of bacterial species and strains. Type IV pilus components have been identified as virulence factors in many pathogenic strains (Craig 2008).

There exists a significant degree of amino acid sequence homology between members of the N-methyl-2 superfamily of different bacterial species. Using the BLAST program (Altschul 1997), proteins with significant homology to *Escherichia coli* PilA, a Type IV pilin and a member of the N-methyl-2 superfamily, can be found in species of *Acinetobacter, Brenneria, Citrobacter, Cronobacter, Dickeya, Edwardsiella, Enterobacter, Erwinia, Haemophilus, Klebsiella, Pantoea, Pasteurella, Pectobacterium, Photorhabdus, Plautia, Proteus, Providencia, Pseudomonas, Rahnella, Salmonella, Serratia, Shigella, Vibrio, Yersinia*, and many other genera.

This homology makes members of the N-methyl-2 superfamily attractive targets for the development of cross-reactive antibodies that could be used to identify the presence of any bacteria bearing a member of the N-methyl-2 superfamily. Alternatively, antibodies that recognize epitopes restricted to a particular subset of bacteria can be used to identify the presence of that specific subset of bacteria without cross-reactivity with irrelevant bacteria that may be present.

The presence of members of the N-methyl-2 superfamily on the surface of bacteria enables rapid assay methods without lengthy sample preparation steps. These proteins are also notable for being present in high copy numbers per cell (Mattick 2002), enabling very sensitive detection of a relatively small number of bacteria.

B. Antibodies

In some particular embodiments, "antibody" as used herein includes intact immunoglobulin molecules, fragments of immunoglobulins, aptamers, and polypeptides that have been engineered to have an antibody-like binding site, which are capable of binding an epitope of any type of target molecule. Any type of antibody known in the art can be generated to bind specifically to an epitope of N-methyl-2 superfamily proteins.

An antibody is an immunoglobulin which possesses the ability to combine with an antigen. It comprises at least two heavy (H) chains and two light (L) chains inter-connected by disulfide bonds. Non-limiting examples of antibodies include monoclonal antibodies (e.g., full length or intact monoclonal antibodies), polyclonal antibodies, multivalent antibodies, and multispecific antibodies (e.g., bi-specific antibodies as long as they exhibit the desired biological activity). An antibody can be affinity-matured.

The term "antibody fragment" comprises only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody. For example, such an antibody fragment may comprise an antigen-binding arm linked to a sequence capable of conferring stability to the fragment.

An "isolated" or "purified" antibody is one which has been identified and separated or recovered, or both, from a component of its natural environment. Contaminant components of an isolated antibody's natural environment are materials that would interfere with diagnostic uses of the antibody. Non-limiting examples of such contaminants include enzymes, hormones, and other proteinaceous or non-proteinaceous solutes. In some embodiments, for example, the antibody may be purified to greater than 95% by weight of protein as determined by the Lowry method, and sometimes more than 99% by weight. Isolated antibody includes the antibody in situ within recombinant cells because at least one component of the antibody's natural environment will not be present. Ordinarily, however, isolated antibody will be prepared by at least one purification step.

The terms "monoclonal antibody" or "monoclonal antibody composition" as used herein refer to a preparation of antibody molecules of single molecular composition. A monoclonal antibody composition displays a single binding specificity and affinity for a particular epitope. The monoclonal antibodies herein specifically include "chimeric" antibodies in which a portion of the heavy or light chain, or both, is identical with or homologous to corresponding sequences in antibodies derived from a particular species or belonging to a particular antibody class or subclass, while the remainder of the chain or chains are identical with or homologous to corresponding sequences in antibodies derived from another species or belonging to another antibody class or subclass, as well as fragments of such antibodies so long as they exhibit the desired biological activity.

"Single-chain Fv" or "scFv" antibody fragments comprise the $V_H$ and $V_L$ domains of antibody, wherein these domains are present in a single polypeptide chain. Generally, the scFv polypeptide further comprises a polypeptide linker between the $V_H$ and $V_L$ domains which enables the scFv to form the desired structure for antigen binding.

An "antigen" is a predetermined substance to which an antibody can selectively bind. The target antigen may be polypeptide, carbohydrate, nucleic acid, lipid, hapten or other naturally occurring or synthetic compound. In some embodiments herein, the relevant antigen is any member protein of the N-methyl-2 superfamily, occurring as either 1) a single protein in solution, 2) a constituent of a complex of proteins, 3) a constituent of a fragment of a cell, or 4) an intact cell.

An "epitope" is the portion of the antigen to which the antibody selectively binds. For a polypeptide antigen, the epitope is generally a peptide portion of about four to ten amino acids.

A "cross-reactive antibody", as used herein, is an antibody that can bind to multiple proteins that differ in primary amino acid sequence. Cross-reactive antibodies bind to multiple proteins having related amino acid sequences, yet do not bind to other proteins with sufficiently distinct amino acid sequences or proteins having sufficiently modified compositions, for example by chemical modification. Cross-reactive antibodies may be polyclonal or monoclonal, aptamers, or fragments including Fab, Fab', F(ab')2, and Fv. Examples of cross-reactive antibodies were known even in the early work on antibodies (Landsteiner 1962). As one example, the field of tissue histocompatibility typing was developed using cross-reactive polyclonal antibodies that bound to overlapping sets of homologous but variable major histocompatibility complex (MHC) determinants (Histocompatibility Testing: Report of a Conference and Workshop. Washington D.C.: National Academy of Sciences—National Research Council, 1965.) Later work determined specific sequences bound by each polyclonal antibody and defined the cross-reactivity profile of each antibody at the amino acid sequence level (Dupont 1988) It was found that, in many cases, a single amino acid substitution abrogated binding by some cross-reactive antibodies, while in other cases a variety of substitutions had negligible effects on binding. Similar results were also demonstrated for cross-reactive monoclonal antibodies to MHC determinants (Parham 1981).

1. General Methods for the Production of Antibodies and Nucleic Acids Encoding Antibodies Antibodies binding to N-methyl-2 superfamily proteins can be produced by a variety of methods known to those skilled in the art, including immunization with intact N-methyl-2 superfamily proteins purified from native sources or from recombinant DNA expression systems, immunization with synthetic peptides representing epitopes of N-methyl-2 superfamily proteins, genetic immunization with sequences encoding N-methyl-2 superfamily proteins or fragments thereof, and immunization with bacteria expressing N-methyl-2 superfamily proteins or subcellular preparations thereof (Harlow 1988).

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. One or more additional booster injections may be given. The process of boosting and titering is repeated until a suitable titer is achieved. When a desired level of immunogenicity is obtained, the immunized animal can be bled and the serum isolated and stored, and/or the animal can be used to generate monoclonal antibodies.

In particular embodiments the antibodies of the invention are monoclonal antibodies. Monoclonal antibodies of the present invention can be produced by a variety of techniques, such as by conventional monoclonal antibody methodology using standard somatic cell hybridization techniques and viral or oncogenic transformation of B lymphocytes.

Monoclonal antibodies may be obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. The monoclonal antibodies of the invention can be made using a hybridoma method, or may be made by recombinant DNA methods well-known to those of ordinary skill in the art.

In the hybridoma method, a mouse or other appropriate host animal is immunized to elicit lymphocytes that produce or are capable of producing antibodies that will specifically bind to the antigen used for immunization. Antibodies may generally be raised in animals by multiple subcutaneous (sc) or intraperitoneal (ip) injections of the antigen and an adjuvant. The antigen may be prepared using methods well-known in the art. For peptide antigens, a carrier may be used to increase the effectiveness of eliciting antibodies to the peptide. Exemplary carriers are keyhole limpet hemocyanin (KLH), bovine serum albumin (BSA, ovalbumin, mouse serum albumin and rabbit serum albumin). Entire cells or subcellular preparations may also be used as antigens for immunization. As also is well known in the art, the immunogenicity of a particular immunogen composition can be enhanced by the use of non-specific stimulators of the immune response, known as adjuvants (Bennett 1992).

Following immunization, somatic cells with the potential for producing antibodies, specifically B lymphocytes (B cells), are selected for use in the monoclonal antibody-generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized. Any one of a number of myeloma cells may be used, as are known to those of skill in the art. For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in the presence of an agent or agents (chemical or electrical) that promote the fusion of cell membranes.

The viable, fused hybrids may be differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

Hypoxanthine aminopterm thymidine (HAT) may be used as a selection medium. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then serially diluted and cloned into individual antibody-producing cell lines, which clones can then be propagated indefinitely to provide monoclonal antibodies. The cell lines may be exploited for monoclonal antibody production using any method known to those of ordinary skill in the art. In one example, a sample of the hybridoma can be injected (often into the peritoneal cavity) into an animal (e.g., a mouse). The injected animal develops tumors secreting the specific monoclonal antibody produced by the fused cell hybrid. The body fluids of the animal, such as serum or ascites fluid, can then be tapped to provide monoclonal antibodies in high concentration. The individual cell lines could also be cultured in vitro, where the monoclonal antibodies are naturally secreted into the culture medium from which they can be readily obtained in high concentrations.

In some embodiments, lymphocytes may be immunized in vitro. Lymphocytes then are fused with myeloma cells using a suitable fusing agent, such as polyethylene glycol, to form a hybridoma cell.

The hybridoma cells thus prepared may be seeded and grown in a suitable culture medium that preferably contains one or more substances that inhibit the growth or survival of the unfused, parental myeloma cells. Culture medium in which hybridoma cells are growing is assayed for production of monoclonal antibodies. The binding specificity of monoclonal antibodies produced by hybridoma cells may be determined be techniques well-known to those in the art, such as by immunoprecipitation or by an in vitro binding assay (e.g., radioimmunoassay (RIA) or enzyme-linked immunosorbent assay (ELISA) or chemiluminescent immunoassay (CLIA)). The binding affinity of the monoclonal antibody can, for example, be determined by a Scatchard analysis. After hybridoma cells are identified that produce antibodies of the desired specificity, affinity, and/or activity, the clones may be subcloned by limiting dilution procedures and grown by standard methods.

The antibodies of the invention can be made by using combinatorial libraries, such as a phage display library, to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. In a certain embodiment, the antibodies are produced in bacteria and the library is screened using phage display to identify the antibody with a high affinity to the antigen.

Monoclonal antibodies produced by any means may be further purified, if desired, using any technique known to those of ordinary skill in the art, such as filtration, centrifugation and various chromatographic methods such as FPLC or affinity chromatography or any other method known to those of ordinary skill in the art.

Nucleic acids encoding antibody gene fragments may be obtained from immune cells harvested from humans or animals. If a library biased in favor of specific clones is desired, the subject is immunized with the antigen to generate an antibody response, and spleen cells and/or circulating B cells or other peripheral blood lymphocytes (PBLs) are recovered for library construction. Additional enrichment for specifically reactive cell populations can be obtained by using a suitable screening procedure to isolate B cells expressing specific membrane bound antibody. Alternatively, the use of spleen cells and/or B cells or other PBLs from an unimmunized donor provides a better representation of the possible antibody repertoire, and also permits the construction of an antibody library using any animal (human or non-human) species in which the antigen is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, etc. Nucleic acid encoding antibody variable gene segments are recovered from the cells of interest and amplified.

Nucleic acid sequence encoding a polypeptide can be designed using the amino acid sequence of the desired region of the polypeptide. Alternatively, the cDNA sequence (or fragments thereof) may be used. DNAs encoding the polypeptide can be prepared by a variety of methods known in the art. Following construction of the DNA molecule encoding the polypeptide, the DNA molecule is operably linked to an expression control sequence in an expression vector, such as a plasmid, wherein the control sequence is recognized by a host cell transformed with the vector. Suitable vectors for expression in prokaryotic and eukaryotic host cells are known in the art. Optionally, the DNA encoding the polypeptide is operably linked to a secretory leader sequence resulting in secretion of the expression product by the host cell into the culture medium. Host cells are transfected and preferably transformed with the expression or cloning vectors of this invention and cultured in conventional nutrient media modified as appropriate for inducing promoters, selecting transformants, or amplifying the genes encoding the desired sequences.

The purified polypeptide can be attached to a suitable matrix such as agarose beads, acrylamide beads, glass beads, cellulose, various acrylic copolymers, hydroxyl methacrylate gels, polyacrylic and polymethacrylic copolymers, nylon, neutral and ionic carriers, and the like, for use in the affinity chromatographic separation of phage display clones. Alternatively, the protein can be used to coat the wells of adsorption plates, expressed on host cells affixed to adsorption plates or used in cell sorting, or conjugated to biotin for capture with streptavidin-coated beads, or used in any other art-known method for panning phage display libraries. The phage library samples are contacted with the immobilized protein under conditions suitable for binding of at least a portion of the phage particles with the adsorbent. Normally, the conditions, including pH, ionic strength, temperature and the like are selected to mimic physiological conditions. The phages bound to the solid phase are washed and then eluted. Moreover, the enriched phages can be grown in bacterial culture and subjected to further rounds of selection.

DNA encoding the hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells.

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In a preferred embodiment, a Fv clone derived from human variable DNA is fused to human constant region DNA to form coding sequence(s) for all human, full or partial length heavy and/or light chains.

DNA encoding the antibody derived from a hybridoma of the invention can also be modified, for example, by substituting the coding sequence for human heavy- and light-chain constant domains in place of homologous murine sequences derived from the hybridoma clone. DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

2. Antibody Fragments

In some embodiments, the present invention encompasses antibody fragments. In certain circumstances there are advantages of using antibody fragments, rather than whole antibodies.

Non-limiting examples of antibody fragments include Fab, Fab', Fab'-SH and F(ab')2 fragments of the antibodies provided herein. These antibody fragments can be created by traditional means, such as enzymatic digestion, or may be generated by recombinant techniques. These fragments are useful for the diagnostic purposes set forth below.

Various techniques may be used for the production of antibody fragments. Traditionally, these fragments were derived via proteolytic digestion of intact antibodies, such as with pepsin or papain and/or by cleavage of disulfide bonds by chemical reduction. However, these fragments can now be produced directly by recombinant host cells. For example, Fab, Fv and ScFv antibody fragments can all be expressed in and secreted from E. coli, thus allowing the facile production of large amounts of these fragments. Alternatively, monoclonal antibody fragments encompassed by the present invention can be synthesized using an automated peptide synthesizer.

Antibody fragments can be isolated from the antibody phage libraries discussed above. Alternatively, Fab'-SH fragments can be directly recovered from E. coli and chemically coupled to form F(ab')2 fragments. According to another approach, F(ab')2 fragments can be isolated directly from recombinant host cell culture. Other techniques for the production of antibody fragments will be apparent to the skilled practitioner. In other embodiments, the antibody of choice is a single chain Fv fragment (scFv). Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. The antibody fragment may also be a "linear antibody." Such linear antibody fragments may be monospecific or bispecific.

3. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody may comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. In some embodiments, the multivalent antibody comprises (or consists of) three to about eight, but preferably four, antigen binding sites. The multivalent antibody comprises at least one polypeptide chain (and preferably two polypeptide chains), wherein the polypeptide chain(s) comprise two or more variable domains.

4. Antibody Derivatives

The antibodies of the present invention can be further modified to contain additional moieties that are known in the art and readily available. In some embodiments, these moieties serve as signal means. For example, in some embodiments, the moieties suitable for derivatization of the antibody are fluorescein, rhodamine, and other fluorescing substances. Other moieties that may serve as signal means include enzymes such as peroxidase and alkaline phosphatase, colored moieties such as colloidal metal particles, dye-containing latex microspheres, and dye-containing liposomes, radioactive moieties such as $I^{125}$, and quantum dots. In other embodiments, the additional moieties may serve as labels to be bound by ligands thereof. Non-limiting examples of labels include biotin, other compounds of molecular mass <5000 including short peptides, and proteins. Non-limiting examples of ligands binding to such labels include streptavidin and antibodies capable of binding to the respective label. A variety of linkers may be used to covalently bind moieties to antibodies, including bispecific linkers N-succinimidyl 6-maleimidocaproate and 6-maleimidocaproic acid hydrazide. In general, the number and/or type of moieties used for derivatization can be determined based on considerations including, but not limited to, the particular properties or functions of the antibody to be improved, whether the antibody derivative will be used in a detection assay under defined conditions, etc.

C. Aptamers

Aptamers are nucleic acid molecules that may be engineered through repeated rounds of in vitro selection to bind to various targets including, for example, proteins, nucleic acids, cells, tissues, and organisms. Because of their specificity and binding abilities, aptamers have great potential as diagnostic agents. In some cases, aptamers have been shown to be better diagnostic agents than other molecules, such as antibodies. An additional advantage of using aptamers is that mass production does not require either animal or cultured cells. Aptamer synthesis may be conducted through Polymerase Chain Reaction ("PCR") or oligonucleotide synthesis, and the resulting aptamers are stable at room temperature and have a long shelf life.

Development of aptamers is typically done through SELEX (Systematic Evolution of Ligands by Exponential Enrichment) or variations on the SELEX process. The SELEX process has been described by Turek and Gold, 1990, and in U.S. Pat. Nos. 5,270,163 and 5,475,096, which are incorporated herein by reference. Variations on the SELEX process, such as photo-SELEX, counter-SELEX, chemi-SELEX, chimeric-SELEX, blended-SELEX, and automated-SELEX, have also been reported. Through SELEX, a large population of oligonucleotides is allowed to interact with the target of interest (e.g., a bacteria cell or a protein isolated from the surface of a bacteria cell). Molecules which bind to the target (termed successful) are separated from those that do not bind through one of several techniques. For example, aptamer bound targets may be removed from the population through binding to nitrocellulose, affinity chromatography, etc. The bound aptamers may then be amplified by PCR.

To facilitate the use of the aptamers for diagnostic purposes, the aptamers may be bound to some form of label for visualization. A number of different labels may be used for this purpose such as fluorophores, chromophores, radiophores, enzymatic tags, antibodies, chemiluminescence, electroluminescence, affinity labels, biosensor, or molecular beacons. The method of visualization may differ depending on whether or not the bacterial detection is to be carried out in vivo or in vitro. In one embodiment, aptamers may be bound to carbon nanotubes, which can fluoresce in the near infra red region when excited with red light. The outer surface of single-walled carbon nanotubes may be functionalized, enabling them to modulate their emission when specific biomolecules are adsorbed. In certain embodiments, dyes or fluorophores may be incorporated into the aptamer or encapsulated in lipid bilayers with an aptamer bound to the outside of the bilayer. In some aspects, a quencher molecule may also be incorporated into the aptamer or encapsulated in lipid bilayers with an aptamer bound to the outside of the bilayer. Binding of the labeled aptamer to its specific bacteria will allow for visualization.

An approach involves the multiplexing of microspheres. Microspheres, such as those from Luminex Corporation or Bio-Rad, may be coupled to specific aptamers. Each type of bacteria-specific aptamer would be coupled to a bead having slightly different fluorescent properties. Mixtures of bead/aptamers would then be incubated with the suspected infected sample. Bacteria would bind to their specific aptamers. A second incubation with, for example, biotinylated aptamers would allow visualization following streptavidin incubation. The beads may be "read" in a dual laser, flow cytometer. A classification laser would allow classification of the bead-aptamer type. The second, reporter laser would allow quantification of the bacteria present, via reading of the intensity of the streptavidin signal.

D. Screening Methods

Embodiments further comprise methods for identifying an antibody capable of binding a protein in the N-methyl-2 superfamily. These assays may comprise screening of large libraries of candidate substances; alternatively, the assays may be used to focus on particular classes of compounds selected with an eye towards structural attributes that are believed to make them more likely to bind a protein in the N-methyl-2 superfamily.

By screening, it is meant that one may assay a series of candidate substances for the ability to bind a protein in the N-methyl-2 superfamily. To identify an antibody with this property, as is used in some embodiments, one generally will perform an immunoassay using a preparation known to comprise known proteins of the N-methyl-2 superfamily, fragments thereof, or synthetic constructs comprising particular epitopes thereof. Examples of preparations that can be used include purified native or recombinant PilA; intact bacterial cells known to express PilA or homologs thereof; membrane-enriched subcellular fractions of bacterial cells known to express PilA or homologs thereof; synthetic peptides representing amino acid sequences found in one or more specific proteins of the N-methyl-2 superfamily; and mixtures of the above.

This immunoassay will further comprise methods to detect the occurrence of binding between a candidate antibody and the said preparation. Examples of methods useful in identifying antibodies having bound a protein in the N-methyl-2 superfamily include: ELISA, RIA, CLIA, fluorescence assays, and label-free binding assays wherein unbound antibody is removed by washing steps and only antibodies which have bound to a target protein remain attached to a solid support. Many analogous methods are known by those of moderate skill in the art. Analogous methods can also be used to identify suitable antibody fragments, including scFv, and aptamers.

The same screening methods can also be used to identify cross-reactive antibodies with desired specificities for proteins of the N-methyl-2 superfamily from different bacterial strains and species. One example is a method of selecting monoclonal antibodies capable of binding to PilA of both *E. coli* and *Pseudomonas aeruginosa* from hybridomas derived from mice immunized with PilA of *E. coli*. The first part of this method is screening the culture medium from each hybridoma by ELISA using microtiter plates coated with *E. coli*, selecting only clones whose culture medium contained antibodies binding to *E. coli*. In the second part, the culture medium from the *E. coli*-binding clones is screened by the same method on microtiter plates coated with *Pseudomonas aeruginosa*, selecting those clones whose culture medium contained antibodies binding to *Pseudomonas aeruginosa*. Finally, antibody from selected clones is purified and used in Western blotting of cell lysates of both *E. coli* and *Pseudomonas aeruginosa*, and clones are selected for producing antibodies binding to a single entity of apparent molecular mass of ~14 kilodaltons, corresponding to PilA. Hybridoma clones screened in this manner produce monoclonal antibodies binding to PilA of both *E. coli* and *Pseudomonas aeruginosa*.

Those of moderate skill in the art recognize that other sequential screening methods and other assay formats may also be used to achieve substantially identical results, that mice immunized with other antigens can also be used to produce equivalent monoclonal antibodies, and that these methods can be applied to selecting cross-reactive antibodies binding to proteins of the N-methyl-2 superfamily from a variety of bacterial strains and species.

Conversely, antibodies can be screened to select for binding to proteins of the N-methyl-2 superfamily from some bacterial strains and species but not others. One example is a method of selecting monoclonal antibodies capable of binding to PilA of *E. coli*, but not of *Pseudomonas aeruginosa*, from hybridomas derived from mice immunized with PilA of *E. coli*. The first part of this method is screening the culture medium from each hybridoma by ELISA using microtiter plates coated with *E. coli*, selecting only clones whose culture medium contained antibodies binding to *E. coli*. In the second part, the culture medium from the *E. coli*—binding clones is screened by the same method on microtiter plates coated with *Pseudomonas aeruginosa*, selecting those clones whose antibodies do not bind to *Pseudomonas aeruginosa*. Finally, antibody from selected clones is purified and used in Western blotting of cell lysates of both *E. coli*, and clones are selected for producing antibodies binding to a single entity of apparent molecular mass of ~14 kilodaltons, corresponding to PilA. Hybridoma clones screened in this manner produce monoclonal antibodies binding to PilA of *E. coli*, but not to PilA of *Pseudomonas aeruginosa*.

E. Antibodies Capable of Binding to Bacteria

Both polyclonal and monoclonal antibodies capable of binding to bacteria are known. Historically, bacteria have been identified and classified based on the host antibody response to bacterial antigens, giving rise to the "serotype" nomenclature of sub-species classification. As an example, *Escherichia coli* isolates have been classified by the reactivity of various antisera, with antigenic groupings termed H, O, and K (Orskov 1992; Orskov 1977). Pathogenesis and other aspects of individual isolates have been related to their serotype (Evans 1983)—*E. coli* O157:H7, for example, is known as a particularly pathogenic strain of enterotoxic *E. coli* (Doyle 1991). The number of recognized bacterial serotypes is very high—*E. coli* alone have at least 50,000-100,000 known serotypes (Orskov 1992). Studies of individual serotype markers have enabled clinical diagnosticians to distinguish pathogenic bacteria from closely related strains, and remain a cornerstone of sub-species identification.

Generally, polyclonal antibodies binding to bacteria have been produced by immunizing an animal with intact bacterial cells bearing a great variety of potential antigens and epitopes. Other methods include immunization with chemically treated bacteria, for example formalin-fixed bacteria, subcellular preparations of bacterial outer membranes and cell walls, and purified lipopolysaccharides purified from bacterial cells. To increase specificity for a particular set of bacteria, polyclonal antibodies have been further fractionated by a variety of methods including affinity chromatography using the bacterial targets of interest.

Monoclonal antibodies binding bacteria have been produced by analogous immunization methods. Examples of commercially available monoclonal antibodies capable of binding bacteria include at least 20 anti-lipopolysaccharide monoclonal antibodies listed in one of many commercial catalogs (Meridian Life Sciences, Inc., Memphis, Tenn., available on the world wide web at meridianlifescience.com/). Other examples include monoclonal antibodies CH1801, CH1802, CH1803, CH1804, CH1805, CH1806, CH1807, CH1808, CH1809, CH1810, CH1811, CH1812, CH1813, CH1814, CH1815, and CH1816 (Silver Lake Research, Monrovia, Calif.). These antibodies were generated by immunizing mice with intact heat-killed or formalin-fixed bacteria, performing fusions to generate hybridomas, and then screening for clones producing monoclonal antibodies capable of binding to particular species of bacteria in ELISA assays using immobilized bacterial cells as the capture antigen. Some antibodies, including CH1809 and CH1813, were also shown to bind to intact live bacterial cells in liquid suspension by immunofluorescence on cell ELISA assays.

Some of these monoclonal antibodies were shown to bind to one bacterial strain or species but not a closely related neighbor, demonstrating the specificity of expression of the relevant epitopes by these bacteria. Other monoclonal antibodies can bind to epitopes that are more broadly expressed. For example, anti-lipopolysaccharide monoclonal antibody 5F4 (Meridian Life Sciences, Inc., Memphis, Tenn.) binds to *Legionella pneumophila* Philadelphia 1 strain, but not to *Legionella pneumophila* strains of serotypes 2, 6, 7, 10, and 11, or to other *Legionella* species. Another anti-lipopolysaccharide monoclonal antibody, T14, binds to a much broader range of *Legionella pneumophila* serotypes, but not to bacteria of other genera (Meridian Life Sciences, Inc., Memphis, Tenn.).

Similarly, CH1801 binds to *Bacteriodes thetaiotaomicron* but not *Bacteroides fragilis*, but CH1803 binds to both *Bacteriodes thetaiotaomicron* and *Bacteroides fragilis*.

Other monoclonal antibodies can bind to an even broader range of bacterial strains and species. Monoclonal antibodies CH1811, CH1812, CH1813, CH1814, CH1815, and CH1816 can bind to bacteria from a range of genera, including *Escherichia, Pseudomonas*, and *Klebsiella*.

In many cases, the composition or identity of the exact structure or structures recognized by polyclonal or monoclonal anti-bacteria antibodies has not been determined or cannot be determined. For example, in Western blots using bacterial lysates of *Escherichia coli*, monoclonal antibodies CH1811 and CH1813 bound to at least four distinct entities of apparent molecular mass of 25-150 kilodaltons. This observation is consistent with these monoclonal antibodies binding to a determinant that is shared by many distinct proteins, although it is not certain which of these proteins may be present on the surface of the bacteria. Monoclonal antibodies CH1812, CH1814, CH1815, and CH1816 bound to no specific entities at all on Western blots of bacterial lysates of *Escherichia coli*, indicating that the entities bound by these monoclonal antibodies may be either 1) carbohydrate-containing moieties not amenable to detection by Western blotting, 2) have conformation-dependent epitopes that are degraded in the Western blot procedure, or 3) are only present on the surface of cells when bacteria are intact. It is also possible that these monoclonal antibodies are essentially non-discriminate, binding to unknown features without apparent compositional similarity, as has been described in the literature for some antibodies (Serban 1985; Laster 1987; Muso 1987; Pisetsky 1989). None of the monoclonal antibodies CH1801, CH1802, CH1803, CH1804, CH1805, CH1806, CH1807, CH1808, CH1809, CH1810, CH1811, CH1812, CH1813, CH1814, CH1815, and CH1816 had binding characteristics consistent with being capable of binding to proteins of the N-methyl-2 superfamily.

F. Devices

In some embodiments, the present invention provides devices that are useful to detect and/or visualize one or more biomarkers from a sample. These devices may comprise a surface and at least one agent that is specific to a desired biomarker. The surface may be any surface to which the desired agents may be attached, including but not limited to a microplate or a lateral flow immunoassay test strip. In some embodiments, the device includes a solid support that contains a sample application zone and a capture zone.

The agent specific to the biomarker may be any agent that can bind specifically to the desired biomarker. Examples include, but are not limited to, aptamers, ligands, antibodies, peptide sequences or other binding agents known to those having skill in the art.

The lateral flow immunoassay (LFA) is a particular embodiment that allows the user to perform a complete immunoassay within 10 minutes or less (Wong 2009, incorporated herein by reference in its entirety). Those skilled in the art know many embodiments and variations of the lateral flow format, including: a variety of porous materials including nitrocellulose, polyvinylidene difluoride, paper, and fiber glass; a variety of test strip housings; colored and fluorescent particles for signal detection including colloidal metals, sols, and polymer latexes; a variety of antibody labels, binding chemistries, and antibody analogs; and other variations. Any embodiment of the lateral flow assay may be used for detection of N-methyl-2 superfamily proteins.

Various known formats exist for immunochromatographic test strips for detecting analytes in liquid samples. One format of LFA uses a direct binding "sandwich" assay, wherein the analyte is bound by two specific binding molecules, the most common type of which is an antibody. Examples of this format are described in U.S. Pat. No. 4,861,711; H. Friesen et al. (1989), which discloses a solid-phase diagnostic device for the determination of biological substances; U.S. Pat. No. 4,740,468; L. Weng et al. (1988) which discloses a solid phase specific binding method and device for detecting an analyte; U.S. Pat. No. 4,168,146; A. Grubb et al. (1979) which discloses a solid phase method and strip with bound antibodies and U.S. Pat. No. 4,435,504; R. Zuk (1984) which discloses a chromatographic immunoassay employing a ligand-binding molecule and a label conjugate. In one type of this format, described in U.S. Pat. No. 4,959,307; J. Olson (1990), the result is revealed as two lines (positive result) or one line (negative result). Each Of these references is incorporated herein by reference in its entirety.

A "testing substrate" is made of a porous material that is generally hydrophilic or capable of being rendered hydrophilic, including inorganic powders such as silica, magnesium sulfate, and alumina; natural polymeric materials such as cotton, particularly cellulosic materials and materials derived from cellulose, such as fiber containing papers, e.g., filter paper, chromatographic paper, etc.; synthetic or modified naturally occurring polymers, such a nitrocellulose, cellulose acetate, fiberglass, poly(vinyl chloride), polyacrylamide, cross-linked dextran, agarose, polyacrylate, etc.; either used by themselves or in conjunction with other materials; ceramic materials; and the like. Alternatively, the testing substrate is fashioned from non-bibulous lateral flow material. For some embodiments, the testing substrate materials are chosen that allow the assay to complete within three minutes of application of the liquid sample.

The shape of the solid support can be that of longitudinal strips, a series of parallel strips, or that of a circular configuration, wherein the circular configuration can optionally be divided into various sections. For the latter configuration, see U.S. Pat. No. 5,141,875, incorporated by reference herein.

The testing substrate, the chromatographic test strip, may be a porous material having pores of at least about $0.1\mu$ to about $10.0\mu$, which is susceptible to traversal by an aqueous medium in response to capillary force. Such materials are generally hydrophilic or are capable of being rendered hydrophilic and include inorganic powders such as silica, magnesium sulfate, and alumina; natural polymeric materials such as cotton, particularly cellulosic materials and materials derived from cellulose, such as fiber containing papers, e.g., filter paper, chromatographic paper, etc.; synthetic or modified naturally occurring polymers, such a nitrocellulose, cellulose acetate, fiberglass, poly(vinyl chloride), polyacrylamide, cross-linked dextran, agarose, polyacrylate, etc.; either used by themselves or in conjunction with other materials; ceramic materials; and the like. The testing substrate should not interfere with the signal reagent. This porous material can be attached to rigid or semi-rigid backing. On the other hand, the porous material may provide its own support. The porous material may be polyfunctional or be capable of being polyfunctionalized to permit covalent bonding of members of a ligand-receptor pair, as well as to permit bonding of any other components that are part of the device.

Further examples of the porous testing substrate of the present invention may be found in assays described, for example, in U.S. Pat. Nos. 4,861,711 and 5,591,645, European Patent Publication No. 291,194 and 323,605, each of which is incorporated herein by reference.

Alternatively, the testing substrate of the present invention is fashioned from non-bibulous lateral flow material. By "non-bibulous" lateral flow is meant liquid flow in which all of the dissolved or dispersed components of the liquid are carried at substantially equal rates and with relatively unimpaired flow laterally through the membrane, as opposed to preferential retention of one or more components as would occur, for example, in materials capable of adsorbing or "imbibing" one or more components. "Bibulous" materials include paper, nitrocellulose, nylon and the like, which have the capability to effect a chromatographic separation of the contained materials.

An example of the non-bibulous testing substrate material in which capillary, non-bibulous lateral flow occurs is glass fiber filter, manufactured by a number of suppliers including Whatman PLC of Maidstone, UK. This material has a typical thickness of 0.1-1 mm a density of 25-800 g/m2, and a flow rate of <100 sec/5 cm. There are many other types of materials that have been used for capillary non-bibulous lateral flow, including cellulose, surface-modified cellulose, polyethylene, polyvinyl chloride, polyvinyl acetate, copolymers of vinyl acetate and vinyl chloride, polyamide, polycarbonate, polystyrene, and other polymers. Membranes formed by the classical phase inversion process may also be used. Thus, the non-bibulous solid supports, in general, will be constructed of an inert material and will optimally be less than 1 mm in thickness and allow a capillary flow rate of <100 sec/5 cm.

Bibulous materials can be converted to those which exhibit nonbibulous flow characteristics by the application of blocking agents, in particular certain detergents and proteins, which obscure the interactive forces that account for the bibulous nature of the supports per se. Thus, nonbibulous solid support materials can be comprised of bibulous materials which have been blocked. Preferred blocking agents include bovine serum albumin, either per se or in methylated or succinylated form, whole animal sera, such as horse serum or fetal calf serum, and other blood proteins. Other protein blocking agents include casein and non-fat dry milk. Detergent-based blocking agents can also be used.

Other embodiments of non-bibulous solid support are known in the art and can be found, for example, in Pawlak et al., International Patent Application WO 92/12428, and Sargent et al., European Patent Publication No. 296 724 B1, herein incorporated by reference.

The testing substrate can have a sufficient inherent strength to be used without a backing material, or additional strength can be provided by means of additional backing. The testing substrate can be a single structure such as a sheet cut into strips or it can be particulate material bound to a support or solid surface such as found, for example, in thin-layer chromatography.

A backing is used for support of the testing substrate in some embodiments. The backing preferably is water insoluble, non-porous, and rigid and usually will be of the same length and width as the solid support but can be larger or smaller. A wide variety of organic and inorganic materials, both natural and synthetic, and combinations thereof, can be employed provided only that the backing does not interfere with the capillary action of the strip, or non-specifically bind assay components, or interfere with the signal means. Illustrative materials include polyethylene, polypropylene, poly (4-methylbutene), polystyrene, polymethacrylate, poly(ethylene terephthalate), nylon, poly(vinyl butyrate), glass, ceramics, metals, and the like.

The particular dimensions of the testing substrate will be a matter of convenience, depending upon the size of the sample involved, the assay protocol, the means for detecting and measuring the signal, and the like. For example, the dimensions may be chosen to regulate the rate of fluid migration as well as the amount of sample to be imbibed by porous testing substrate.

Optionally, the testing substrate can be partially or fully enclosed in a moisture-impermeable, inert casing that can be transparent, translucent, or opaque, as known in the art. Such a casing ideally has at least two apertures, one above the sample application zone and one above the signal area(s). The aperture above the signal area(s) can be covered with a transparent material. Alternatively, no apertures above the sample receiving zone are necessary if a bibulous means is provided to the exterior of the casing and to the testing substrate below the sample receiving zone such that the sample would be wicked in and applied to the testing substrate. Examples of such casings can be found in European Patent Publication No. 290 194.

One member of a ligand-receptor pair may be non-diffusively bound by direct or indirect means to the solid support. The solid support may have been previously derivatized prior to the application of the second member. The direct binding can be covalent or non-covalent. Covalent binding can be accomplished by using a solid support derivatized with reactive groups such as amino, chloromethyl, aldehyde, carboxyl, epoxy, and the like. Covalent binding can also be accomplished by any method known in the art such as, for example, the use of glutaraldehyde, aminosilanes, cyanogen bromide, carbonyldiimidazole, ethyl chloroformate, 1-(3-nitrobenzyloxy-methyl)-pyridimium chloride (NBPC) and treslyl chloride, as well as other methods described in Chibata 1978; Cutrecasas 1970; March 1974; and Tijssen 1985. The non-covalent binding takes advantage of the natural adhesion of second members to the non-synthetic and especially the synthetic fibers. Thus, appropriately buffered solutions can be mixed with the solid support then evaporated, leaving a coating of the desired member of the ligand-receptor pair on the membrane.

The members of a ligand-receptor pair can be applied to the solid support by a variety of means known in the art. Various "printing" techniques have previously been used for application of such liquid reagents to carriers, for example, microsyringes, pens using metered pumps, direct printing and ink-jet printing, and any of these techniques can be used in the present context. To facilitate manufacture, the solid support can be treated and then subdivided into smaller portions (e.g., small, narrow strips each embodying the required areas and zones) to provide a plurality of identical solid supports. In applying the members to the solid support, it is necessary that the signal zone(s) span the width and the depth of the solvent front created by any fluid traversing through the solid support. Such fluid may be the sample solution, a wicking fluid as described below, or a solution containing the substrate for an enzymatic signal means.

G. Detection Methods

One of ordinary skill in the art knows a variety of methods and devices for the detection and analysis of the biomarkers, and detection of the biomarker presence may be performed in any manner known to those having skill in the art. In some embodiments, the method by which the biomarkers are detected may be related to the type of device used.

The lateral flow immunoassay (LFA) is a particular embodiment that allows the user to perform a complete immunoassay within 10 minutes or less (Wong 2009). Those skilled in the art know many embodiments and variations of the lateral flow format, including: a variety of porous materials including nitrocellulose, polyvinylidene difluoride, paper, and fiber glass; a variety of test strip housings; colored and fluorescent particles for signal detection including colloidal metals, sols, and polymer latexes; a variety of antibody labels, binding chemistries, and antibody analogs; and other variations. Any embodiment of the lateral flow assay may be used for detection of N-methyl-2 superfamily proteins.

In some embodiments, the biomarkers bind to the specific agent on the device. In such embodiments, the bound biomarkers may be detected by any appropriate method known to those having skill in the art. In some embodiments, the presence of the biomarkers may be detected using an immunoassay, an enzyme-linked immunosorbent assay (ELISA), an immunofluorescence assay (IFA), a radioimmunoassay (RIA), a lateral flow chromatographic test, a Western blot, or an immunoprecipitation assay, flow cytometry, or fluorescence microscopy. In some embodiments, the presence of the biomarkers may be detected using colorimetric detection methods. These methods may result in visual color changes that correlate with the presence or absence of the biomarkers. In some embodiments, the presence of the biomarkers may be detected using Mass Spectrometry, Fourier transform infrared spectroscopy (FTIR), Polymerase Chain Reaction (PCR), Quantitative Real-Time PCR, or Northern Blot.

H. Urinary Tract Infections

The Infectious Disease Society of America guidelines define bacterial urinary tract infections (UTIs) by the presence of $>10^5$ CFU/ml of a single pathogen in patient urine (Warren 1999) Bacteriuria, or the presence of bacteria in urine, is assessed by urine culture, a gold-standard laboratory procedure that requires 24-48 hrs to obtain a result.

In some embodiments, provided are methods for detecting bacteria in urine using N-methyl-2 superfamily proteins as a biomarker. Any appropriate assay detection may be used to test the sample. In some embodiments, anti-PilA antibodies are used to construct a lateral flow immunoassay. Other immunoassay formats can also be used, including ELISA, IFA, CLIA, and RIA. In some embodiments, the anti-PilA antibodies recognize PilA from a wide range of Gram-negative bacteria, including strains of *Escherichia coli, Proteus mirabilis, Klebsiella* spp., *Citrobacter* spp., *Providencia* spp., *Pseudomonas* spp., and *Morganella* spp.—all of which are strains known to cause bacterial UTIs. The presence of PilA in urine is indicative of the presence of bacteria in the urine of the patient, and the sensitivity of the immunoassay is equivalent to the accepted diagnostic criteria for UTI.

I. Blood Infections

Sepsis, or septicemia, is a potentially fatal condition most often caused by bacterial infection in the bloodstream. Detection of bacteria in blood, or bacteremia, is therefore a most important diagnostic procedure. Typical diagnosis of bloodstream bacterial infections (bacterial BSI) is done by blood culture (Ryan 2004). Blood culture in a typical clnical setting requires at least 24-48 hrs to obtain a result. Other methods such as polymerase chain reaction (PCR) have not found wide clinical use at this time (Reier-Nilsen 2009). These assays require hours and days to return a result, a major disadvantage when the progression of infection may be rapid and have fatal consequences.

Causative agents of bacterial BSI in humans include a range of Gram-negative and Gram-positive bacteria, with *Staphylococcus aureus* and *E. coli* being the most prevalent in the US (Pfaller 1998). Overall, *E. coli* has been found to be responsible for ~30% of all sepsis cases in the US (Martin 2003). Immunoassays in many formats can be performed rapidly and have sufficient theoretical sensitivity to be used for the detection of bloodstream infections. For example, immunofluorescence assays for the determination of bacterial antigens are known and can visualize single bacterial cells (Moyes 2009). However, such assays have not found clinical use, largely because there is a lack of antibodies with sufficiently broad detection range among the bacteria known to cause BSI.

The inventors describe a novel biomarker for bacterial BSI with both specificity for bacterial cells and sufficient broad-spectrum expression by relevant bacteria. The inventors also describe an immunoassay detecting this biomarker in blood samples from humans or animals. Such immunoassays can be rapid diagnostic methods for bacterial BSI.

Proteins of the N-methyl-2 superfamily proteins are present on most bacterial strains described in the literature as major causative agents of bacterial BSI, including *E. coli* and *S. aureus*. Those skilled in the art know a variety of methods to generate antibodies to N-methyl-2 superfamily proteins, reactive with both *E. coli* and *S. aureus*. For example, PilA, a member of the N-methyl-2 superfamily, is a protein expressed by both *E. coli* and *S. aureus*, as well as many other strains associated with bacteremia. The gene encoding PilA in *E. coli* is known, and can be expressed in commercially available recombinant expression and purification systems widely used for that purpose (e.g., Invitrogen Prokaryotic Expression Guide, Life Technologies, Inc., San Diego, Calif., Cat. # B-1350841). Antibodies to PilA can be generated by immunization of mice or rabbits with purified recombinant PilA (Harlow 1988). Polyclonal antibodies can be expected to cross-react with PilA of any strains because of the high degree of homology between PilA of Gram-positive and Gram-negative strains. Monoclonal antibodies can be selected that bind to both *E. coli* and *S. aureus*, as well as other strains of interest, in immunofluorescence assays. Other methods of antibody generation and screening can also be used to produce suitable antibodies.

Any appropriate assay may be used. In some embodiments, such antibodies can be used in immunofluorescence assays as described by Moyes. Microscopic examination or automated analysis of material reacted with fluorescent label-bearing antibodies to N-methyl-2 superfamily proteins can reveal whether a sample contains cells or cell fragments comprising N-methyl-2 superfamily proteins. The presence of bacteremia can be deduced from the presence of N-methyl-2 superfamily proteins in the sample. Those skilled in the art know of other methods of immunoassay that can also be used to obtain a similar diagnostic result by using antibodies reactive with the instant biomarker, the N-methyl-2 superfamily proteins. For example, such antibodies can be used in lateral flow immunoassays, RIA, ELISA, and CLIA assays to detect bacteria in clinical samples.

J. Bacterial Infections in Humans and Animals

Many epidemiologically significant bacterial infections in humans and animals do not follow clinical courses that allow the collection of samples with high concentrations of causative pathogenic bacteria. Examples include BSI, localized infections that cannot be located by other means, and infections of tissues that cannot be easily sampled by biopsy or other means (Ryan 2004). For such infections, extremely sensitive diagnostic procedures are desirable, capable of detecting a single bacterial cell in a sample. This problem is typically addressed by allowing any bacteria in a sample to grow and multiply on nutrient medium until sufficient numbers of bacteria are available for analytical determination. Such cultures can be performed on solid or liquid nutrient medium.

In some embodiments, an assay that minimizes the time required for detecting the presence of bacteria in a sample is provided by combining 1) the expansion of bacteria by culture and 2) using N-methyl-2 superfamily proteins as a biomarker of the presence of bacteria in cultured samples. Using N-methyl-2 superfamily proteins as a biomarker of the presence of bacteria offers the advantages of 1) providing a single, defined target analyte for detection assays for a large number of bacterial strains, 2) enabling an extremely sensitivity detection assay due to the large number of analyte molecules per targeted bacterial cell, 3) enabling the testing of bacteria expanded through culture in the same way as native, non-expanded samples.

Any appropriate method may be used for expansion of bacteria from clinical samples and any appropriate assay may be used to test the cultured samples. Immunoassay formats that can be used include ELISA, IFA, CLIA, and RIA. Lateral flow immunochromatographic tests can also be used. Those skilled in the art also know that such assays may be useful for any of a large number of clinical microbiology problems, including bloodstream infections, cerebrospinal fluid infections, and other types of clinical samples.

K. Bacterial Contamination of Beverages

In some embodiments, N-methyl-2 superfamily proteins are used as a biomarker of bacterial contamination of beverages. Bacterial contamination of beverages, including fruit juices, milk and milk products, and other liquids intended for human consumption, is a major source of gastrointestinal illnesses and their more serious, sometimes fatal, sequelae. The US Centers for Disease Control has estimated that foodborne pathogens are responsible for approximately 9.4 million cases of illness annually, including over 3 million cases attributable to the top four bacterial pathogens—*Salmonella* spp., *Clostridium perfringens*, *Campylobacter* spp., and *Staphylococcus aureus* (2011 estimates, CDC Estimates of Foodborne Illness in the United States, available on the world wide web at cdc.gov/foodborneburden/2011-foodborne-estimates; Bad Bug Book, Handbook of Foodborne Pathogenic Microorganisms and Natural Toxins, Second Edition. Lampel K A, Al-Khaldi S, Assimon S A, eds. US FDA, 2012). Pathogenic *E. coli*, including enterotoxigenic *E. coli* (ETEC), enteropathogenic *E. coli* (EPEC) enterohemorrhagic *E. coli* (EHEC), enteroinvasive *E. coli* (EIEC), enteroaggregative *E. coli* (EAEC), and diffusely adherent *E. coli* (DAEC), are more prevalent outside the US in locations with poor sanitation.

The presence of any of these pathogenic bacteria in ready-to-drink beverages can lead to an outbreak of serious gastrointestinal illness, and the food industry expends significant efforts to prevent the contamination of beverages by bacterial pathogens. Unfortunately, the most common detection method for bacterial contamination, culture on nutrient medium, is a labor-intensive technique that requires at least one day to obtain a result. A rapid and sensitive method to detect a wide range of enteropathogenic bacteria is highly desired.

In some embodiments, provided are methods for detecting bacteria in a beverage using N-methyl-2 superfamily proteins as a biomarker. Any appropriate assay detection may be used to test the beverage.

L. Bacterial Contamination of Solid Samples

In some embodiments, methods are described using N-methyl-2 superfamily proteins as a biomarker for bacterial contamination of solid samples, such as food. All solid samples may be assayed in an analogous manner. This method comprises 1) using a liquid to suspend potentially present bacteria in a fluid sample, 2) using an immunoassay comprising antibodies capable of binding to N-methyl-2 superfamily proteins to detect bacteria in said fluid sample, and 3) determining the presence of bacteria in the solid food by the presence of N-methyl-2 superfamily proteins in the fluid sample. This method addresses both the problem of rapid detection of potentially pathogenic bacteria and the problem of heterogeneity of solid food.

Bacterial contamination of solid food is a common cause of spoilage and consumption of contaminated food is a common cause of enteric illness. Epidemiology and causative agents of foodborne illness. Bacterial contamination of solid foods presents an additional challenge over beverages—most microbiological detection methods utilize liquid samples and are not compatible with the variety of solid foods that may be desirable to test for bacterial contamination.

Those skilled in the art understand that a variety of liquids may be suitable for the purpose of extracting bacteria from solid samples, that any desired ratio of liquid to solid sample may be used, that a variety of methods may be used to aid in the suspension of bacteria in the liquid, and that a variety of solid samples may be extracted in this manner. It is understood by those in the art that this methodology is applicable to any type of solid food.

Further, because the liquid extraction and immunoassay parts of this method are both rapid and require no instrumentation, it is straightforward for those skilled in the art to provide a rapid test, encompassing both of these procedures in a single kit, for the purpose of on-site determination of bacterial contamination in a variety of solid samples, including foods.

An extraction and immunoassay method, using N-methyl-2 superfamily proteins as a biomarker, can detect bacterial contamination in solid samples. However, the concentration of bacteria in the sample must be relatively high to enable such rapid determination. To adapt this method to determine low concentrations of bacteria in solid samples, the sensitivity of this method may be augmented by any combination of the following steps: 1) using a higher ratio of solid sample to liquid extracting buffer; 2) using a higher-sensitivity immunoassay, such as an immunofluorescence assay, instead of the immunochromatographic test strip; and 3) including a culture step wherein the liquid sample with extracted bacteria is used to inoculate culture medium to expand the number of bacteria present (or the solid sample is extracted directly with liquid culture medium).

M. Use of Biomarker to Detect the Presence of a Specific Bacteria

In some aspects, described are methods of using N-methyl-2 superfamily proteins to determine specific types of bacteria based on the exact epitope of N-methyl-2 superfamily proteins targeted by antibodies generated for this purpose, without regard to the presence or absence of other species or strains—even though these other strains may be far greater in number in a given sample.

For example, some methods may use N-methyl-2 superfamily proteins as a biomarker of the presence of *Pseudomonas* spp. without regard to the presence of *Escherichia* spp. by selecting a specific epitope of a N-methyl-2 superfamily protein, the generation of antibodies to said epitope, and the use of said antibodies in an immunoassay detecting *Pseudomonas* spp. without regard to the presence of *Escherichia* spp.

Both *Pseudomonas* spp. and *Escherichia* spp. are Gram-negative bacteria that may be present, separately or together, in the same sample. In some cases, a specific action may be warranted if a sample contains *Pseudomonas* spp., while no action is warranted if only *Escherichia* spp. are present. For example, *Pseudomonas* may be a more likely cause of recreational water illness when present in swimming pool water than *Escherichia* spp., and *Pseudomonas*-caused illness may be more serious. Therefore it may be reasonable to close and decontaminate a swimming pool if *Pseudomonas* is detected, but not *Escherichia*.

Bacteria of both genera, *Pseudomonas* and *Escherichia*, express Type IV pilins, members of the N-methyl-2 superfamily. However, the sequence VAIIGILAA (SEQ ID NO. 2) is only present in Type IV pilins of *Pseudomonas* spp., and not in any known proteins of *Escherichia* spp. The corresponding sequence in *Escherichia coli* is VIGIIAILS (e.g., NCBI Reference Sequence: ZP_12904468.1) (SEQ ID NO. 3). A BLAST sequence alignment search reveals >250 proteins from *Pseudomonas* spp. containing the exact sequence VAIIGILAA (SEQ ID NO. 2) and no proteins from *Escherichia* spp. containing the same sequence (Stephen 1997). Those skilled in the art can identify such sequences present in N-methyl-2 superfamily proteins of one set of bacteria but not another.

Antibodies to the sequence VAIIGILAA (SEQ ID NO. 2) can be produced by a variety of means known by those skilled in the art. Synthetic peptides containing the sequence VAIIGILAA (SEQ ID NO. 2) can be conjugated to carrier proteins and used as immunogens for generation of antibodies in animals. Alternative methods include immunization with peptide conjugated to non-protein carriers, genetic immunization with sequences that are translated to proteins containing VAIIGILAA (SEQ ID NO. 2), and screening of antibody or other binding protein libraries with probes containing the sequence VAIIGILAA (SEQ ID NO. 2). Another alternative method is screening aptamer libraries with probes containing the sequence VAIIGILAA (SEQ ID NO. 2). Once antibodies, binding proteins, or aptamers, capable of binding VAIIGILAA (SEQ ID NO. 2) have been identified, a second round of screening is performed by a similar method to exclude any such binding molecules that can also bind to VIGIIAILS (SEQ ID NO. 3). A suitable antibody, binding protein, or aptamer can be identified by testing for binding to *Pseudomonas* bacteria expressing Type IV pilins. Any antibody, binding protein, or aptamer derived by this or analogous methodology can be used in immunoassays detecting N-methyl-2 superfamily proteins of *Pseudomonas* but not *Escherichia*.

Immunoassays using specific antibodies, binding proteins, and aptamers are known. Any such assay may be used to detect N-methyl-2 superfamily proteins of *Pseudomonas* in a sample. Detection of N-methyl-2 superfamily proteins of *Pseudomonas* can be interpreted as the presence of *Pseudomonas* spp. in the sample, regardless of the presence of *Escherichia* spp.

It would be readily recognized by persons skilled in the art that this method may be useful to selectively identify any desired bacterial strains, and is not limited to these particular species.

N. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

N-methyl-2 Superfamily Proteins as a Biomarker for Bacteriuria and Urinary Tract Infections This embodiment of the present invention uses bacterial PilA, a member of the N-methyl-2 superfamily, as a biomarker of bacteriuria. A method of using rapid lateral flow immunoassay test detecting PilA for the determination of bacteriuria, with a total test time of under 15 minutes, is described.

In this embodiment, anti-PilA antibodies CH1826 and CH1822 (SLRC, Monrovia, Calif.) are used to construct a lateral flow immunoassay. Monoclonal antibodies CH1826 and CH1822 bind *E. coli, Proteus mirabilis*, and other strains in ELISA assays, and were shown to precipitate a band of approximately 14 kilodaltons from *E. coli* cells in a standard immunoprecipitation assay (Thermo Catalog #26148, performed according to manufacturer's protocols), consistent with binding to PilA from both species. This embodiment uses the particular variation of the lateral flow immunoassay format described in U.S. Pat. No. 7,919,331, incorporated herein by reference in its entirety. Those skilled in the art are aware of many variations of the lateral flow immunoassay format, any of which may be equivalent to the present example.

Purified antibodies CH1826 and CH1822 were biotinylated in accordance with described procedures (Elia 2010). Separately, purified antibodies CH1826 and CH1822 were labeled with streptomycin by a modification of published procedures (Niemeyer 2004). Briefly, streptomycin-EMCH was prepared by adding 25 mg of ε-maleimidocaproic acid hydrazide (Prochem, Rockford, Ill.) to 92 mg of streptomycin sulfate (Sigma Chemical Company, St. Louis, Mo.) in dimethyl formamide and allowed to react for 24 hrs. Purified antibodies CH1826 and CH1822 were reacted with 2-iminothiolane (Sigma Chemical Company, St. Louis, Mo.) at a molar ratio of 1:30 for 1 hr, and 12 mg of streptomycin-EMCH was added. Free reactants were removed by dialysis against phosphate-buffered saline for 48 hrs.

Colloidal gold was prepared in accordance with published procedures (Oliver 2010). Anti-streptomycin monoclonal antibody CH2013 (Silver Lake Research Corporation, Monrovia, Calif.) was adsorbed onto the gold colloid. Anti-streptomycin gold conjugate was suspended in buffer containing 2 mM sodium borate, pH 9.0, 1% bovine serum albumin, and 0.5% Tween-20 detergent, dispensed into cylindrical flat-bottom test vials (Jade Scientific, Westland, Mich.) and dried. Biotinylated and streptomycin-labeled antibodies CH1826 and CH1822 were dispensed into the same vials and dried.

Immunochromatographic lateral flow test strips were prepared as previously described (Millipore Corp 1996; Weiss 1999; Harvey 1999; Keene 1997). Test strip chromatographic media included Hi-Flow plastic-backed nitrocellulose membrane (Millipore Corp., Bedford, Mass.); Hi-Flow glass fiber media (Millipore Corp., Bedford, Mass.), acrylic plastic protective cover (G&L, San Jose, Calif.), and adhesive-coated plastic backing (G&L, San Jose, Calif.). Streptavidin was deposited onto the nitrocellulose portion of a lateral flow immunoassay test strip, serving as a "test line" of a typical lateral flow assay format. Polyclonal goat antiserum to mouse immunoglobulins (GAM-Ig; American Qualex, Temecula, Calif.) was deposited at the "control line" of the same nitrocellulose, in a position downstream from the streptavidin relative to the flow of sample through the strip.

In the test procedure, 250 μl of a sample is dispensed in the vial with dried gold conjugate and antibodies, and allowed to incubate for 5 minutes to allow rehydration of dried reagents. During this time, labeled CH1826 and CH1822 antibodies bind to any PilA in the sample, and anti-streptomycin-coated gold conjugate is able to bind to the streptomycin-labeled CH1826 and CH1822. Following the incubation, the test strip is placed in the vial so that the fiberglass portion was in contact with the sample. Migration of sample through the test strip, driven by wicking action, allows all reagents to come into contact with the test line. Here, streptavidin is capable of capturing biotinylated CH1826 and CH1822, thereby capturing any gold conjugate particles that are bound to the biotinylated anti-PilA antibodies via PilA polymers and streptomycin-labeled anti-PilA. Therefore, the appearance of a colored (red or pink) line at the test line is an indication that PilA is present in the sample. The control line captures gold conjugate particles via binding of GAM-Ig to any adsorbed or bound antibody, and a red control line indicates the test ran correctly. The results of the test are determined visually 10 minutes after placing the test strip in the vial. The presence of any visible color at the test line indicates a positive result, and the absence of color at the test line indicates a negative result. Absence of a control line indicates an invalid test.

An alternative embodiment of this test is made by using a traditional lateral flow immunoassay test strip format, as generally taught by U.S. Pat. No. 4,376,110. Purified antibody CH1822 is directly coated onto colloidal gold particles in accordance with published procedures (Oliver 2010). Purified antibody CH1826 is deposited at the test line of the lateral flow test strip membrane, and GAM-Ig is deposited on the control line. CH1822-gold conjugate particles are allowed to bind to any bacteria present in a urine sample. The sample is then allowed to flow through the membrane of the test strip, transporting any CH1822-gold-bacteria complexes over the test line. Immobilized antibody CH1826 captures these complexes by binding to the bacteria, resulting in the appearance of a red test line. The GAM-Ig at the control line captures CH1822-gold conjugate particles that have traversed the test line, resulting in a red control band that indicates that the test has been run correctly.

The use of this embodiment was demonstrated on normal urine spiked with varying concentrations of *Escherichia coli*, the pathogen responsible for most urinary tract infections worldwide. Sterile-filtered urine from normal donors was spiked with cultured *E. coli* strain J96, originally isolated from a patient with urinary tract infection (American Type Culture Collection, Rockville, Md.; strain 700336). Samples were tested by urine culture (Tille. P. M. (2013). Bailey & Scott's Diagnostic Microbiology (13th ed.). Mosby/Elsevier. ISBN: 978-0323083300), and by the method described in this Example 2. The results are shown in Table 1.

TABLE 1

Results of testing urine samples with urine culture and with lateral flow immunoassay test strips with CH1826 and CH1822 anti-PilA antibodies

| SAMPLE | URINE CULTURE RESULT (CFU/ml) | LATERAL FLOW TEST RESULTS |
|---|---|---|
| 1 | 0 | Negative |
| 2 | $1 \times 10^2$ | Negative |
| 3 | $4 \times 10^2$ | Negative |

TABLE 1-continued

Results of testing urine samples with urine culture
and with lateral flow immunoassay test strips
with CH1826 and CH1822 anti-PilA antibodies

| SAMPLE | URINE CULTURE RESULT (CFU/ml) | LATERAL FLOW TEST RESULTS |
|---|---|---|
| 4 | $6 \times 10^2$ | Negative |
| 5 | $3 \times 10^3$ | Positive |
| 6 | $2 \times 10^2$ | Negative |
| 7 | 0 | Negative |
| 8 | $4 \times 10^3$ | Positive |
| 9 | $1 \times 10^5$ | Positive |
| 10 | $2 \times 10^5$ | Positive |
| 11 | $7 \times 10^4$ | Positive |
| 12 | $4 \times 10^4$ | Positive |
| 13 | $7 \times 10^3$ | Negative |
| 14 | $8 \times 10^4$ | Positive |
| 15 | $1 \times 10^3$ | Negative |
| 16 | $7 \times 10^5$ | Positive |
| 17 | $3 \times 10^5$ | Positive |
| 18 | $1 \times 10^5$ | Positive |
| 19 | $1 \times 10^6$ | Positive |
| 20 | $3 \times 10^6$ | Positive |
| 21 | $7 \times 10^5$ | Positive |
| 22 | $5 \times 10^5$ | Positive |
| 23 | $2 \times 10^4$ | Positive |
| 24 | $6 \times 10^2$ | Negative |
| 25 | $1 \times 10^5$ | Positive |

The results indicate that this embodiment is capable of detecting *E. coli* in urine with an apparent limit of detection of $<1 \times 10^4$ CFU/ml. This method correlates very well with the current clinical gold standard assay for bacteria in urine. Therefore, PilA, an N-methyl-2 superfamily protein, is a valid and valuable biomarker for the presence of bacteria in urine and for diagnosis of urinary tract infections.

Example 2

N-methyl-2 Superfamily Proteins as a Biomarker of Blood-borne Bacterial Infection Blood is collected from patients using aseptic technique according to standard clinical practice (Versalovic 2011). Two or three blood samples are taken from each patient to maximize detection capability.

For each blood sample, an immunofluorescence assay is performed using antibodies binding to bacterial Type IV pilins, members of the N-methyl-2 superfamily. In the preferred embodiment, F(ab')2 fragments of two monoclonal antibodies are used, CH1822 and CH1826.

Each antibody is prepared for use in the assay by 1) purification of intact monoclonal antibody, 2) preparation of F(ab')2 fragments by published methods (Harlow 1988), and 3) conjugation of each F(ab')2 fragment to fluorescein isothiocyanate (FITC) by described methods (Wisdom 1994). Many other types of fluorescent dyes can be used, including rhodamine, Alexa fluor, and cyanines FITC-conjugated antibodies are stored at 4° C. in the dark prior to use in the assay.

A volume of 2-10 ml of each blood sample is used for the assay. Two to 10 micrograms of each FITC-conjugated CH1822 F(ab')2 and FITC-conjugated CH1826 F(ab')2 is added to each sample and incubated at 4° C. for 30 minutes, protected from light. The sample is then centrifuged at 10,000×g for 10 minutes and the supernatant discarded. The pellet is resuspended in 1 ml of 1M ammonium chloride to lyse the remaining erythrocytes. After 1 minute, 10 ml of wash buffer (phosphate-buffered saline, 1% bovine serum albumin) is added and the sample centrifuged again as above. The supernatant is discarded and the pellet resuspended in 10 ml of wash buffer. The sample is centrifuged as above and the supernatant removed. The pellet is resuspended in 20-100 microliters of wash buffer.

The solution is analyzed by fluorescence microscopy. If any bacteria are present, a localized fluorescent signal will be seen. Alternatively, the sample can be analyzed by an automated flow cytometer, such as FACSCalibur (BD Biosciences, San Jose, Calif.), gated on bacterial cells. Both methods can be used to enumerate the number of bacteria in the analyzed volume and therefrom to calculate the concentration of bacteria in the original blood sample.

The detection of the biomarker, Type IV pilins, proteins of the N-methyl-2 superfamily, is thus an indicator of the presence of bacteria in the original blood sample. The immunofluorescence assay can be completed in approximately 1.5 hrs, an important advantage over blood cultures that can require several days to obtain a result.

Example 3

N-methyl-2 Superfamily Proteins as a Biomarker of Other Bacterial Infections in Humans or Animals Sterile bovine serum was used as a standardized sample matrix. Those skilled in the art appreciate that clinical samples from humans or animals comprising serum, other blood fractions, whole blood, non-blood biological fluids, or solid tissue samples suspended or homogenized in liquid, can all serve as analogous test samples for the described assay.

Sterile serum samples were spiked with cultured *E. coli* (American Type Culture Collection, Rockville, Md.; strain 25922) at approximate concentrations of 0, 0.1, 1, 10, 100, and 1000 CFU/ml. One milliliter of each spiked sample was added to 9 ml of Luria-Bertani broth in a 100 ml flask (BD Falcon, Franklin Lakes, N.J.). All flasks were cultured with aeration and shaking at 37° C. Volumes of 0.5 ml were removed from flasks at different time intervals for testing.

Immunochromatographic test strips were prepared using monoclonal antibodies CH1822 and CH1826, which bind to the protein PilA, a member of the N-methyl-2 superfamily. Monoclonal antibodies CH1822 and CH1826 bind to *E. coli, Pseudomonas aeruginosa,* and other strains in ELISA assays, and were shown to precipitate a band of approximately 14 kilodaltons from *E. coli* cells in a standard immunoprecipitation assay (Thermo Catalog #26148, performed according to manufacturer's protocols), consistent with binding to PilA from both species.

Lateral flow test strips were produced as generally described in Example 1. Purified antibody CH1826 was deposited at the test line of the strip, and GAM-Ig was deposited at the control line. Purified antibody CH1822 was adsorbed onto colloidal gold particles in accordance with published procedures (Oliver 2010).

Each sample of cultured bacteria was diluted 1:1 with buffer containing 100 mM Tris, pH 9.0, 1% bovine serum albumin, 0.2% polysorbate-20, 0.1% fish skin gelatin (all buffer components from Sigma Chemical, St. Louis, Mo.). Twenty microliters of CH1822-colloidal gold conjugate was added to 250 microliters of diluted culture, and allowed to incubate for 5 minutes. A test strip having CH1826 at the test line was inserted into the sampe, allowing the sample to travel through the test strip by capillary action. Test procedure was followed and results were determined and interpreted as in Example 1.

Results, presented in Table 2, indicate that an immunochromatographic test detecting PilA, a member of the N-methyl-2 superfamily can be used to determine the presence of bacteria in a cultured sample. Further, the test procedure can be used to determine the presence of bacteria in the original sample. Under the described conditions, a sample of 1 ml containing ~1 viable bacterium can be identified as having bacteria in ~4 hrs. This time frame offers significant advantages to clinicians and patients, compared with today's standard of care.

TABLE 2

Results of Testing Cultured Bacteria Samples with Immunochromatographic Test Strips Detecting N-methyl-2 superfamily Proteins

| Bacteria in Spiked Sample (CFU/ml) | Test Results At 2 hr Culture Time (POSITIVE/ TOTAL TESTED) | Test Results At 4 hr Culture Time (POSITIVE/ TOTAL TESTED) | Test Results At 6 hr Culture Time (POSITIVE/ TOTAL TESTED) | Test Results At 8 hr Culture Time (POSITIVE/ TOTAL TESTED) |
|---|---|---|---|---|
| 0 (Negative Control) | 0/3 | 0/3 | 0/3 | 0/3 |
| E. coli 0.1 CFU/ml | 0/3 | 0/3 | 0/3 | 0/3 |
| E. coli 1 CFU/ml | 0/3 | 3/3 | 3/3 | 3/3 |
| E. coli 10 CFU/ml | 1/3 | 3/3 | 3/3 | 3/3 |
| E. coli 100 CFU/ml | 2/3 | 3/3 | 3/3 | 3/3 |
| E. coli $10^3$ CFU/ml | 3/3 | 3/3 | 3/3 | 3/3 |

This Example demonstrates the usefulness of N-methyl-2 superfamily proteins as a biomarker of the presence of bacteria in cultured samples from clinical samples of minimal bacterial concentration (1 viable organism).

Example 4

N-methyl-2 Superfamily Proteins as a Biomarker of Bacterial Contamination of Beverages In this Example, monoclonal antibody CH1822 (SLRC, Monrovia, Calif.) was selected for broadly cross-reactive binding to Type IV pilins, members of the N-methyl-2 superfamily. Immunochromatographic tests strips were constructed as in Example 1, except indirect immunogold particles were used in place of dyed polystyrene latex particles. Colloidal gold was prepared according to published procedures derived from the Turkevich method (Turkevich 1951; Frenz 1973; Slot 1985) and conjugated to purified CH1822 by previously described methods (Oliver 2010). CH1822-gold particles were resuspended in buffer containing 2 mM borate, pH 9.0, 1% bovine serum albumin, and 0.1% polysorbate 20 (Sigma Chemical, St. Louis, Mo.) and used directly in the lateral flow assay. Test strips were prepare as in Example 1, using CH1822 purified antibody at the test line.

Pasteurized orange juice from a local market (Minute Maid® No Pulp Orange Juice) was spiked with *Salmonella enterica* (ATCC, Rockville, Md., strain #8326) or *Escherichia coli* (ATCC, Rockville, Md., strain #8739) at approximate concentrations of 0, 10, $10^2$, $10^3$, $10^4$, $10^5$, and $10^6$ CFU/ml. One hundred fifty microliters of each prepared spiked sample was pH-adjusted to pH 8.0 with 1N NaOH and diluted 1:1 with buffer containing 100 mM Tris pH 8.0, 2% BSA, and 0.5% polysorbate 20. Twenty microliters of CH1822 gold particles were added to each sample and mixed thoroughly. A test strip with CH1822 test line and GAM-Ig control line was inserted into each sample and incubated 10 minutes at room temperature. The appearance of a red color at the test line indicated a positive result, and absence of color at the test line indicated a negative result. The absence of color at the control line indicated an invalid test.

The results are shown in Table 3. Juice samples containing more than $10^4$ CFU/ml of either strain of bacteria yielded a positive result, and samples containing less than $10^3$ CFU/ml of either strain of bacteria yielded a negative result. This experiment indicates that a rapid test of this type can be used to detect bacterial contamination in liquid beverages, and that N-methyl-2 superfamily proteins are a valid biomarker for bacterial contamination of beverages.

TABLE 3

Detection of bacterial contamination of fruit juice by an immunoassay detecting N-methyl-2 superfamily proteins

| SAMPLE | TEST RESULTS (POSITIVE/TOTAL TESTED) |
|---|---|
| Negative Control (0 CFU/ml) | 0/6 |
| E. coli $10^6$ CFU/ml | 3/3 |
| E. coli $10^5$ CFU/ml | 3/3 |
| E. coli $10^4$ CFU/ml | 3/3 |
| E. coli $10^3$ CFU/ml | 1/3 |
| E. coli $10^2$ CFU/ml | 0/3 |
| E. coli $10^1$ CFU/ml | 0/3 |
| S. enterica $10^6$ CFU/ml | 3/3 |
| S. enterica $10^5$ CFU/ml | 3/3 |
| S. enterica $10^4$ CFU/ml | 3/3 |
| S. enterica $10^3$ CFU/ml | 0/3 |
| S. enterica $10^2$ CFU/ml | 0/3 |
| S. enterica $10^1$ CFU/ml | 0/3 |

Example 5

N-methyl-2 Superfamily Proteins as a Biomarker of Bacterial Contamination of Solid Samples Fresh ground beef was used as the solid food. Fresh chuck roast from a local market was trimmed of outside surface layers and ground with a manual meat grinder (Weston, Strongsville, Ohio) that was previously sterilized by autoclaving.

*Salmonella enterica* (ATCC, Rockville, Md., strain #8326) was cultured on agar and 15 colonies of ~1 mm diameter were collected. This bacterial sample was mixed with 250 g ground beef using a spatula. This spiked sample was assumed to contain a highly variable concentration of bacteria.

One gram samples of spiked and non-spiked ground beef were collected from different sections of a bowl of ground beef. Each sample was placed in a 12×75 mm test tube, and 1 ml of buffer containing 100 mM Tris, pH 9.0, 1% bovine serum albumin, and 0.2% polysorbate-20 was added to each tube. Each tube was agitated by vortexing for 2 minutes. Immunochromatographic test strips, prepared using anti-Type-IV-pilin monoclonal antibody CH1822 as described for Example 4 above, were placed into each tube and results determined as described for Example 4 above. The results are shown in Table 4.

TABLE 4

Detection of bacterial contamination of solid food by an
immunoassay detecting N-methyl-2 superfamily proteins

| SAMPLE | TEST RESULTS (POSITIVE/TOTAL TESTED) |
| --- | --- |
| Unspiked Ground Beef | 0/10 |
| S. enterica Spiked Ground Beef | 10/10 |

These results demonstrate that N-methyl-2 superfamily proteins can be used as a biomarker of bacterial contamination of solid foods and other solid samples. Despite the probable heterogeneity of bacterial concentrations in solid samples, a suitable extraction method can yield a sufficiently high concentration of extracted bacteria to produce a reliable result with an immunoassay detecting N-methyl-2 superfamily proteins.

Example 6

Using N-methyl-2 Superfamily Proteins as a Biomarker of the Presence of Specific Bacteria This Example describes a method of detecting specific species or strains of bacteria, regardless of the presence of bacteria of other strains or species, by using antibodies specific to sequences of proteins of the N-methyl-2 superfamily that are only expressed by those bacteria which are to be detected. In this embodiment, the bacteria to be detected are of the genus *Pseudomonas*, and the antibodies used do not bind to *E. coli* and other bacteria of the genus *Escherichia*. Antibodies used in this Example bind to the sequence VAIIGILAA (SEQ ID NO. 2), which is present in Type IV pilins of *Pseudomonas* spp., but not in any proteins in *Escherichia* spp., as determined by BLAST analysis. The homologous region of Type IV pilins of *Escherichia* spp. has the sequence VIGIIAILS (SEQ ID NO. 3). Type IV pilins are proteins of the N-methyl-2 superfamily.

In this Example, the detection method is demonstrated on samples of swimming pool water. *Pseudomonas* spp. may cause more serious recreational water illness than *E. coli*, although the latter is more prevalent. Swimming pool operators may choose to close and disinfect a pool when *Pseudomonas* spp. is present, but not when *E. coli* is detected.

Monoclonal antibodies are made by immunizing mice with synthetic peptide having the sequence VAIIGILAA (SEQ ID NO. 2), conjugated to the carrier keyhole limpet hemocyanin (KLH) at the amino terminus. Serum samples from immunized mice are tested by ELISA for binding to VAIIGILAA (SEQ ID NO. 2) conjugated to bovine serum albumin (BSA). Splenocytes from mice producing antibodies binding to VAIIGILAA-BSA (SEQ ID NO. 2) are used for fusions to generate hybridomas. Hybridoma clones are selected for producing monoclonal antibodies specifically binding to VAIIGILAA-BSA (SEQ ID NO. 2). These clones are then tested for binding to VIGIIAILS-BSA (SEQ ID NO. 3), and those clones producing antibodies that bind VIGIIAILS-BSA (SEQ ID NO. 3) are discarded. Remaining clones are further tested for reactivity in ELISA with intact *Pseudomonas aeruginosa* and non-reactive clones discarded. The remaining clones produce monoclonal antibodies with the defined specificity of binding to Type IV pilins of *Pseudomonas aeruginosa* but not to Type IV pilins of *Escherichia* spp. This specificity may be confirmed by Western blotting of lysates of *Pseudomonas aeruginosa* and *E. coli*.

Monoclonal antibodies selected in this manner are used to produce lateral flow immunochromatographic test strips, as described in Example 3. The same antibody is used to produce colloidal gold conjugates and to deposit on the test line of the test strip.

Test vials are prepared by depositing 50 microliters of a sterile solution containing 100 mM Tris, pH 8.0, 5% sucrose, 3% BSA, 0.5% polysorbate-20, and 1% fish skin gelatin into flat-bottomed polypropylene vials and drying at 60° C. for 24 hrs.

In the test procedure, 250 microliters of swimming pool water is deposited into the test vial and allowed to rehydrate the components dried therein. Twenty microliters of colloidal gold-antibody conjugate is added to the vial. A test strip produced as above is inserted into the vial, allowing the liquid therein to travel through the strip by capillary action. The test strip results are determined and interpreted as in Examples 1 and 3. The presence of red color at the test line indicates the presence of *Pseudomonas* spp. in the swimming pool water.

This embodiment demonstrates that specific bacteria can be detected by using proteins of the N-methyl-2 superfamily as biomarkers. Those moderately skilled in the art will recognize that analogous methods can be used to produce antibodies for the detection of a variety of distinct sets of bacteria, exclusive of other sets, based on sequence differences in known proteins of the N-methyl-2 superfamily expressed by the two sets. Those moderately skilled in the art will also recognize that analogous assay methods can be used for the detection of specific sets of bacteria in a variety of liquid and solid samples, including body fluids from human or animals, water, beverages, and solid samples.

\* \* \*

All of the compositions and/or methods disclosed and claimed herein can be made and executed without undue experimentation in light of the present disclosure. While the compositions and methods of this invention have been described in terms of some embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references and any others listed herein, to the extent that they provide exemplary procedural or other details supplementary to those set forth herein, are specifically incorporated herein by reference in their entirety.

Altschul, *Nucleic Acids Res.* 25:3389-3402, 1997
Bennett, et al., *J Immunol Meth.* 153:31-40, 1992
Bennett, et al., *Lett App Microbiol.* 22: 237-243, 1996
Chibata, "Immobilized Enzymes." Halstead Press, NY (1978)
Craig, et al., *Curr Opin Struct Biol* 18(2):267-77, 2008
Cutrecasas, *J. Bio. Chem.,* 245:3059, 1970
Doyle, *Int J Food Microbiol.* 12(4):289-301, 1991

Dupont B, ed. Immunobiology of HLA. Histocompatibility Testing 1987, Vol. I, and Immunogenetics and Histocompatibility, Vol II. Springer-Verlag, New York, 1988.
Elia, *Current Protocols in Protein Science* 3.6.1-3.6.21, 2010
European Patent Publication No. 290 194
European Patent Publication No. 291,194
European Patent Publication No. 323,605
Evans, et al., *Rev Infect Dis.* 5 Suppl 4:S692-701, 1983
Frens, *Phys. Sci.* 241:20-22, 1973
Harlow E, Lane D, *Antibodies: A Laboratory Manual* (Cold Spring Harbor, N.Y.: CSHL Press, 1988
Harvey, *Optimization of Nitrocellulose Membrane Based Immunoassays* NH: Schleicher & Schuell, 1991
Histocompatibility Testing Report of a Conference and Workshop. Washington D.C.: National Academy of Sciences—National Research Council, 1965
Keene, *Guide to Building Molecular and Immunodiagnostic Device Platforms* NH: Schleicher & Schuell, 1997
Kim & Doyle, *Appl. Env. Microbiol.* 58:1764-1767, 1992
Landsteiner K. The Specificity of Serological Reactions, rev. edn. New York: Dover, 1962
Laster, et al., *Clin Immunol Immunopathol.* 44(2):187-205, 1987
March et al., *Anal. Biochem.*, 60:149, et seq, 1974
Marchler-Bauer, et al. *Nucleic Acids Res.* 39(D) 225-9, 2011
Martin, et al., *N Engl J Med.* 348:1546-1554, 2003
Mattick, *Annu Rev Microbiol.* 56:289-314, 2002
Millipore Corp., *Short Guide for Developing Immunochromatographic Test Strips* Bedford, Mass., 1996
Moyes, *Current Protocols in Microbiology.* 15:A.3K.1-A.3K.13, 2009
Muso & Jacob, *Clin Immunol Immunopathol.* 42(3):370-4, 1987
Niemeyer. Bioconjugation Protocols: Strategies and Methods. Humana Press, NJ. 2004
Oliver C. Preparation of colloidal gold. *Methods Mol Biol* 2010; 588:363
Orskov I, et al., *Bacteriol Rev.* 41(3):667-710, 1977
Orskov, et al., *Can J Microbiol.* 38(7):699-704, 1992
Parham & Brodsky, *Hum Immunol.* 3(4):277-99, 1981
Pfaller, et al., *Antimicrob Agents Chemother.* 42(7):1762-70, 1998
Pisetsky, et al., *J Immunol.* 143(11):3609-13, 1989
Reier-Nilsen, et al., *BMC Pediatr.* 19; 9:5, 2009
Ryan K J; Ray CG (editors) (2004). *Sherris Medical Microbiology* (4th ed.). McGraw Hill
Ryan, *Sherris Medical Microbiology* (4th ed.). McGraw Hill, 2004
Serban, et al., *J Immunol.* 135(5):3122-7, 1985
Sigrist, et al., *Nucleic Acids Res.* 38(Database issue) 161-6, 2010
Slot & Geuze, *Eur. J. Cell Biol.* 38:87-93, 1985
Stephen, et al., *Nucleic Acids Res.* 25:3389-3402, 1997
Tijssen et al., Practice and Theory of Enzyme Immunoassays, Chapter 3, Elsevier Science Publishers, (1985)
Turkevich, et al., *Discuss Faraday Soc.* 11:55-75, 1951
U.S. Pat. No. 4,168,146
U.S. Pat. No. 4,435,504
U.S. Pat. No. 4,740,468
U.S. Pat. No. 4,861,711
U.S. Pat. No. 4,959,307
U.S. Pat. No. 5,141,875
U.S. Pat. No. 5,591,645
U.S. Pat. No. 7,919,331
Versalovic, J, ed. Manual of Clinical Microbiology, $10^{th}$ ed. ACM Press; 2011. Online edition
Warren, et al., *Clin Infect Dis.* 29(4):745-58, 1999.
Weiss, IVD Technology, 48, 1999
Wisdom, *Methods in Molecular Biology.* 295:131-4, 1994
WO 92/12428
Wong R, Tse H, eds. "Lateral Flow Immunoassay" Humana Press, New York, N.Y. 2009

What is claimed is:

1. A method of detecting the presence of bacteria in a sample comprising:
   (a) contacting the sample with an antibody, fragment thereof, aptamer or ligand capable of binding one or more proteins in the N-methyl-2 superfamily that are present on more than one species of bacteria to form one or more complexes in the presence of said N-methyl-2 superfamily proteins, if any, in the sample, wherein the protein in the N-methyl-2 superfamily comprises a conserved domain having the amino acid sequence of [KRHEQSTAG]-G-[FYLIVM]-[ST]-[LT]-[LIVP]-E-[LIVMFWSTAG] (SEQ ID NO. 1); and
   (b) detecting the presence of the one or more said complexes,
wherein the presence of at least one complex indicates the presence of bacteria.

2. The method of claim 1, wherein the antibody is polyclonal or monoclonal.

3. The method of claim 1, wherein the sample is a liquid sample.

4. The method of claim 3, wherein the liquid sample is urine, blood, serum, blood products, plasma, saliva, body fluid, water, culture medium, diluted culture medium, petroleum product, fuel, liquid undergoing fermentation, or a beverage.

5. The method of claim 1, wherein the sample is a solid sample.

6. The method of claim 5, wherein the solid sample is human or animal tissue, stool, sputum, expectorate, an agricultural product, food, solids collected by centrifugation or filtration, soil, or sediment.

7. The method claim 5, wherein the solid sample is partially or completely solubilized by addition of liquid.

8. The method of claim 1, wherein the sample is obtained from a human or an animal.

9. The method of claim 1, wherein said antibody fragment is selected from the group consisting of a single-chain Fv, an Fab, an Fab', and an F(ab')2.

10. The method of claim 1, wherein the antibody, fragment thereof, or aptamer is labeled.

11. The method of claim 10, wherein the label is biotin, an enzyme, a latex particle, a metal colloid particle, a fluorescent dye, a quantum dot, or a carbon nanotube.

12. The method of claim 1, wherein the detecting is performed by an immunoassay, an enzyme-linked immunosorbent assay (ELISA), an immunofluorescence assay (IFA), a radioimmunoassay (RIA), a chemiluminescence immunoassay (CLIA), a lateral flow chromatographic test, a Western blot, an immunoprecipitation assay, flow cytometry, or fluorescence microscopy.

13. The method of claim 1 wherein the one or more antibodies are immobilized on a solid support.

14. The method of claim 13, wherein the solid support is a particle, a bead, a plastic or glass surface, a porous membrane, an array, or a chip.

15. The method of claim 13 wherein the solid support forms part of an assay device.

16. The method of claim 15 wherein the assay device is a lateral flow immunoassay device.

17. The method of claim 1, wherein the bacteria is of a genus or genera selected from the group consisting of *Bacillus, Clostridium, Pseudomonas, Xanthomonas, Vibrio, Bacteroides, Escherichia, Klebsiella, Salmonella, Shigella, Erwinia, Rickettsia, Chlamydia, Mycoplasma, Actinomyces, Streptomyces, Mycobacterium, Micrococcus, Staphylococcus, Lactobacillus, Diplococcus, Streptococcus, Proteus, Citrobacter, Providencia, Morganella, Campylobacter, Gardnerella,* and *Borrelia.*

18. The method of claim 1, wherein the antibody is CH1822 or CH1826.

19. A method of detecting bacterial contamination in a sample comprising:
   (a) contacting the sample with an antibody, fragment thereof, aptamer or ligand capable of binding one or more proteins in the N-methyl-2 superfamily that are present on more than one species of bacteria to form one or more complexes in the presence of said N-methyl-2 superfamily proteins, if any, in the sample, wherein the protein in the N-methyl-2 superfamily comprises a conserved domain having the amino acid sequence of [KRHEQSTAG]-G-[FYLIVM]-[ST]-[LT]-[LIVP]-E-[LIVMFWSTAG](SEQ ID NO. 1); and
   (b) detecting the one or more said complexes,
wherein the presence of at least one complex indicates the presence of a contaminating concentration of bacteria.

20. A method of identifying the presence of one or more specific bacteria in a sample comprising:
   (a) contacting the sample with an antibody, fragment thereof, aptamer or ligand capable of binding one or more identified proteins of the N-methyl-2 superfamily expressed by a subset of bacteria but not by other bacteria to form one or more complexes in the presence of the one or more specific N-methyl-2 superfamily proteins, if any, in the sample, wherein the protein in the N-methyl-2 superfamily comprises a conserved domain having the amino acid sequence of [KRHEQSTAG]-G-[FYLIVM]-[ST]-[LT]-[LIVP]-E-[LIVMFWSTAG] (SEQ ID NO. 1); and
   (b) detecting the presence of the one or more said complexes,
wherein the presence of at least one complex indicates the presence of the one or more specific bacteria.

21. The method of claim 20, wherein the antibody is polyclonal or monoclonal.

22. The method of claim 20, wherein the sample is a liquid sample.

23. The method of claim 22, wherein the liquid sample is urine, blood, serum, blood products, plasma, saliva, body fluid, water, culture medium, diluted culture medium, petroleum product, fuel, liquid undergoing fermentation, or a beverage.

24. The method of claim 20, wherein the sample is a solid sample.

25. The method of claim 24, wherein the solid sample is human or animal tissue, stool, sputum, expectorate, an agricultural product, food, solids collected by centrifugation or filtration, soil, or sediment.

26. The method of claim 24, wherein the solid sample is partially or completely solubilized by addition of liquid.

27. The method of claim 20, wherein the sample is obtained from a human or an animal.

28. The method of claim 20, wherein said antibody fragment is selected from the group consisting of a single-chain Fv, an Fab, an Fab', and an F(ab')2.

29. The method of claim 20, wherein the antibody, fragment thereof, or aptamer is labeled.

30. The method of claim 29, wherein the label is biotin, an enzyme, a latex particle, a metal colloid particle, a fluorescent dye, a quantum dot, or a carbon nanotube.

31. The method of claim 20, wherein the detecting is performed by an immunoassay, an enzyme-linked immunosorbent assay (ELISA), an immunofluorescence assay (IFA), a radioimmunoassay (RIA), a chemiluminescence immunoassay (CLIA), a lateral flow chromatographic test, a Western blot, an immunoprecipitation assay, flow cytometry, or fluorescence microscopy.

32. The method of claim 20 wherein the one or more antibodies are immobilized on a solid support.

33. The method of 20, wherein the solid support is a particle, a bead, a plastic or glass surface, a porous membrane, an array, or a chip.

34. The method of claim 32 wherein the solid support forms part of an assay device.

35. The method of claim 34 wherein the assay device is a lateral flow immunoassay device.

36. The method of claim 20, wherein the bacteria is of a genus or genera selected from the group consisting of *Bacillus, Clostridium, Pseudomonas, Xanthomonas, Vibrio, Bacteroides, Escherichia, Klebsiella, Salmonella, Shigella, Erwinia, Rickettsia, Chlamydia, Mycoplasma, Actinomyces, Streptomyces, Mycobacterium, Micrococcus, Staphylococcus, Lactobacillus, Diplococcus, Streptococcus, Proteus, Citrobacter, Providencia, Morganella, Campylobacter, Gardnerella*, and *Borrelia*.

* * * * *

SEQUENCE LISTING

```
<160> NUMBER OF SEQ ID NOS: 3

<210> SEQ ID NO 1
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 1

Lys Arg His Glu Gln Ser Thr Ala Gly Gly Phe Tyr Leu Ile Val Met
1               5                   10                  15

Ser Thr Leu Thr Leu Ile Val Pro Glu Leu Ile Val Met Phe Trp Ser
            20                  25                  30

Thr Ala Gly
        35

<210> SEQ ID NO 2
<211> LENGTH: 9
<212> TYPE: PRT
<213> ORGANISM: Pseudomonas aeruginosa

<400> SEQUENCE: 2

Val Ala Ile Ile Gly Ile Leu Ala Ala
1               5
```

```
<210> SEQ ID NO 3
<211> LENGTH: 9
<212> TYPE: PRT
<213> ORGANISM: Escherichia coli

<400> SEQUENCE: 3

Val Ile Gly Ile Ile Ala Ile Leu Ser
1               5
```